US010858697B2

(12) United States Patent
Ozawa et al.

(10) Patent No.: US 10,858,697 B2
(45) Date of Patent: Dec. 8, 2020

(54) NUCLEIC ACID ANALYZER AND NUCLEIC ACID ANALYZING METHOD

(71) Applicant: SYSMEX CORPORATION, Kobe (JP)

(72) Inventors: Toshiyuki Ozawa, Kobe (JP); Masanori Imazu, Kobe (JP); Hironori Kobayashi, Kobe (JP); Nobuhiro Kitagawa, Kobe (JP); Yoshihiko Kitawaki, Kobe (JP)

(73) Assignee: SYSMEX Corporation, Kobe (JP)

( * ) Notice: Subject to any disclaimer, the term of this patent is extended or adjusted under 35 U.S.C. 154(b) by 0 days.

(21) Appl. No.: 16/165,230

(22) Filed: Oct. 19, 2018

(65) Prior Publication Data
US 2019/0048411 A1 Feb. 14, 2019

Related U.S. Application Data

(63) Continuation of application No. PCT/JP2017/007213, filed on Feb. 24, 2017.

(30) Foreign Application Priority Data

Apr. 20, 2016 (JP) .................................. 2016-084854

(51) Int. Cl.
C12Q 1/6848 (2018.01)
B01L 3/00 (2006.01)
(Continued)

(52) U.S. Cl.
CPC .............. *C12Q 1/6848* (2013.01); *B01L 3/52* (2013.01); *B01L 7/52* (2013.01); *C12M 1/00* (2013.01);
(Continued)

(58) Field of Classification Search
None
See application file for complete search history.

(56) References Cited

U.S. PATENT DOCUMENTS 6,632,398 B1 * 10/2003 Nebuloni ............... G01N 21/07
422/64
2005/0064582 A1 * 3/2005 Wittwer ................ B01L 3/5082
435/287.2
(Continued)

FOREIGN PATENT DOCUMENTS

CN 1965073 A 5/2007
CN 102549140 A 7/2012
(Continued)

OTHER PUBLICATIONS

Focke Maximilian et al., "Microstructuring of polymer films for sensitive genotyping by real-time PCR on a centrifugal microfluidic platform", Journal "Lab on a Chip", Oct. 7, 2010, p. 2519-2526, vol. 10, No. 19, RSC Publishing Cited in the International Search Report (ISR) & the International Preliminary Report on Patentability (IPRP) of PCT/JP2017/007213.
(Continued)

Primary Examiner — Kathryn Wright
(74) Attorney, Agent, or Firm — Metrolex IP Law Group, PLLC

(57) ABSTRACT

A nucleic acid analyzer according to one or more embodiments may include a container setting part that sets a second container, a rotation drive part that rotates the container setting part by applying a driving force to a surface of the container setting part, to supply the extraction liquid injected through the injection port to the storages through the flow path by a centrifugal force. A first temperature adjustment part that adjusts a temperature of the second container provided in the container setting part, such that a nucleic acid amplification reaction occurs in the storages, and a (Continued)

detector that detects a nucleic acid amplification reaction which occurs in the storages with the second container provided in the container setting part interposed between the first temperature adjustment part and the detector in a vertical direction.

20 Claims, 22 Drawing Sheets

(51) Int. Cl.
    *B01L 7/00*     (2006.01)
    *G01N 35/00*     (2006.01)
    *C12M 1/00*     (2006.01)
    *C12N 15/09*     (2006.01)

(52) U.S. Cl.
    CPC .......... *G01N 35/00* (2013.01); *B01L 2300/18* (2013.01); *C12N 15/09* (2013.01)

(56) References Cited

U.S. PATENT DOCUMENTS

| | | | |
|---|---|---|---|
| 2007/0009391 A1* | 1/2007 | Bedingham | B01L 3/502715 422/547 |
| 2012/0184025 A1 | 7/2012 | Kawata et al. | |
| 2017/0080419 A1* | 3/2017 | Hori | B01L 3/5023 |

FOREIGN PATENT DOCUMENTS

| | | | | |
|---|---|---|---|---|
| CN | 103026238 A | 4/2013 | | |
| CN | 104145014 A | 11/2014 | | |
| CN | 104950122 A | 9/2015 | | |
| EP | 3351941 A1 | 7/2018 | | |
| JP | 2012-161340 A | 8/2012 | | |
| WO | 2008034896 A2 | 3/2008 | | |
| WO | WO-2015174429 A1 * | 11/2015 | ............ | B01L 3/5023 |

OTHER PUBLICATIONS

The Chinese Office Action dated Mar. 7, 2019 in a counterpart Chinese patent application.
F. Stumpf et al., "LabDisk with complete reagent prestorage for sample-to-answer nucleic acid based detection of respiratory pathogens verified with influenza A H3N2 virus", Lab on a Chip, Jan. 1, 2016, pp. 199-207, vol. 16, No. 1, The Royal Society of Chemistry; Cited in EESR issued on Sep. 26, 2019 in a counterpart European patent application.
G. Czilwik et al., "Rapid and fully automated bacterial pathogen detection on a centrifugal-microfluidic LabDisk using highly sensitive nested PCR with integrated sample preparation", Lab on a Chip, Jan. 1, 2015, pp. 3749-3759, vol. 15, No. 18, The Royal Society of Chemistry; Cited in EESR issued on Sep. 26, 2019 in a counterpart European patent application.
Mark Keller et al., "Automated Forensic Animal Family Identification by Nested PCR and Melt Curve Analysis on an Off-the-Shelf Thermocycler Augmented with a Centrifugal Microfluidic Disk Segment", PLOS One, Jul. 6, 2015, vol. 10(7): e0131845, PLOS; Cited in EESR issued on Sep. 26, 2019 in a counterpart European patent application.
Minghui Tang et al., "A Review of Biomedical Centrifugal Microfluidic Platforms", Micromachines, Feb. 6, 2016, vol. 7(2): 26, MPDI; Cited in EESR issued on Sep. 26, 2019 in a counterpart European patent application.
Mary Amasia et al., "Centrifugal microfluidic platform for rapid PCR amplification using integrated thermoelectric heating and ice-valving", Sensors and Actuators B: Chemical, Nov. 29, 2011, pp. 1191-1197, vol. 161, No. 1, Elsevier; Cited in EESR dated Sep. 26, 2019 in a counterpart European patent application.
Chunsun Zhang et al.,"PCR microfluidic devices for DNA amplification", Biotechnology Advances, May 1, 2006, pp. 243-284, vol. 24, No. 3, Elsevier; Cited in EESR issued on Sep. 26, 2019 in a counterpart European patent application.
Wei Wang et al., "Droplet-based micro oscillating-flow PCR chip", Journal of Micromechanics & Microengineering, Aug. 1, 2005, pp. 1369-1377, vol. 15, No. 8, Institute of Physics Publishing; Cited in EESR issued on Sep. 26, 2019 in a counterpart European patent application.
Jae Hwan Jung et al., "Ultrafast Rotary PCR system for multiple influenza viral RNA detection", Lab on a Chip, Jan. 1, 2012, pp. 1598-1600, vol. 12, The Royal Society of Chemistry; Cited in EESR issued on Sep. 26, 2019 in a counterpart European patent application.
Shunsuke Furutani et al., "Rapid Detection of *Salmonella enterica* in Food Using a Compact Disc-Shaped Device", Micromachines, Jan. 15, 2016, vol. 7(1): 10, MPDI; Cited in EESR issued on Sep. 26, 2019 in a counterpart European patent application.
Guanghui Wang et al., "A lab-in-a-droplet bioassay strategy for centrifugal microfluidics with density difference pumping, power to disc and bidirectional flow control", Lab on a Chip, Jan. 1, 2013, pp. 3698-3706, vol. 13, No. 18, The Royal Society of Chemistry; Cited in EESR issued on Sep. 26, 2019 in a counterpart European patent application.
Baogang Miao et al., "Centrifugal Microfluidic System for Nucleic Acid Amplification and Detection", Sensors, Jan. 1, 2015, pp. 27954-27968, vol. 15, No. 11, MPDI; Cited in EESR issued on Sep. 26, 2019 in a counterpart European patent application.
The extended European search report ("EESR") dated Sep. 26, 2019 in a counterpart European patent application.

* cited by examiner

| GENE | STORAGE | DETECTION TARGET NUCLEIC ACID |
|---|---|---|
| KRAS | C1 | c.34G > T (G12C) |
| | C2 | c.34G > C (G12R) |
| | C3 | c.34G > A (G12S) |
| | C4 | c.35G > C (G12A) |
| | C5 | c.35G > A (G12D) |
| | C6 | c.35G > T (G12V) |
| | C7 | c.38G > A (G13D) |
| | C8 | c.38G > T (G13V) |

NUCLEIC ACID ANALYZER AND NUCLEIC ACID ANALYZING METHOD

CROSS REFERENCE TO RELATED APPLICATIONS

This application is a continuation application of International Application No. PCT/JP2017/007213, filed on Feb. 24, 2017, entitled "NUCLEIC ACID ANALYSIS DEVICE AND NUCLEIC ACID ANALYSIS METHOD", which claims priority based on the Article 8 of Patent Cooperation Treaty from prior Japanese Patent Application No. 2016-084854, filed on Apr. 20, 2016, the entire contents of which are incorporated herein by reference.

BACKGROUND

The disclosure relates to a nucleic acid analyzer and a nucleic acid analyzing method.

In recent years, along with proliferation of genetic tests, a device that performs automatic extraction of nucleic acids to detection of nucleic acids is demanded. International Patent Application Publication No. WO 2008/034896 to Alexandre et al. ("Alexandre") describes a configuration including a disk-shaped reaction container in which multiple PCR (Polymerase Chain Reaction) reaction layers are disposed, a temperature adjustment part that holds the reaction container and adjusts the temperatures of areas of the reaction container to different levels, and a detector that detects a PCR reaction in real time. In addition, Alexandre describes a rotation axis that penetrates the reaction container and the temperature adjustment part for rotating the reaction container. The reaction container is rotated by the rotation axis, and a PCR reaction layer is transported to an area at which a target temperature is set.

For detection of a PCR reaction, it is desirable to adjust the temperature of the reaction container with high accuracy. However, with a configuration in which the rotation shaft penetrates the temperature adjustment part as described above, the reaction container is in contact with outside air, and thus it is difficult to set the temperature of the reaction container to a desired temperature. Also, since the rotation shaft and a mechanism for rotating the rotation shaft are disposed along with the detector and the temperature adjustment part, the configuration of the device becomes complicated.

SUMMARY

A nucleic acid analyzer that analyzes nucleic acid according one or more embodiments may include a reaction container including an injection port through which extraction liquid containing nucleic acids is injected, storages that store reagents for amplifying the nucleic acids, and a flow path that connects the storages and the injection port, a container setting part that the reaction container, a rotation drive part that rotates the container setting part by applying a driving force to a surface of the container setting part, to supply the extraction liquid injected through the injection port to the storages through the flow path by a centrifugal force, a first temperature adjustment part that adjusts a temperature of the reaction container provided in the container setting part, such that a nucleic acid amplification reaction occurs in the storages, and a detector that detects a nucleic acid amplification reaction which occurs in the storage with the reaction container interposed between the first temperature adjustment part and the detector in a vertical direction.

A nucleic acid analyzing method according one or more embodiments may include positioning a reaction container, in which extraction liquid containing nucleic acids has been injected through an injection port, in a container setting part, rotating the container setting part by applying a driving force to a surface of the container setting part, to supply the extraction liquid injected through the injection port to storages through the flow path by a centrifugal force, adjusting a temperature of the reaction container provided in the container setting part by a first temperature adjustment part which is disposed on one of upper and lower sides of the reaction container set in the container setting part, such that the nucleic acid amplification reaction occurs in the storages, and detecting a nucleic acid amplification reaction in response to temperature adjustment by a detector disposed on the other of the upper and lower sides of the reaction container provided in the container setting part.

DETAILED DESCRIPTION

Figure 1:
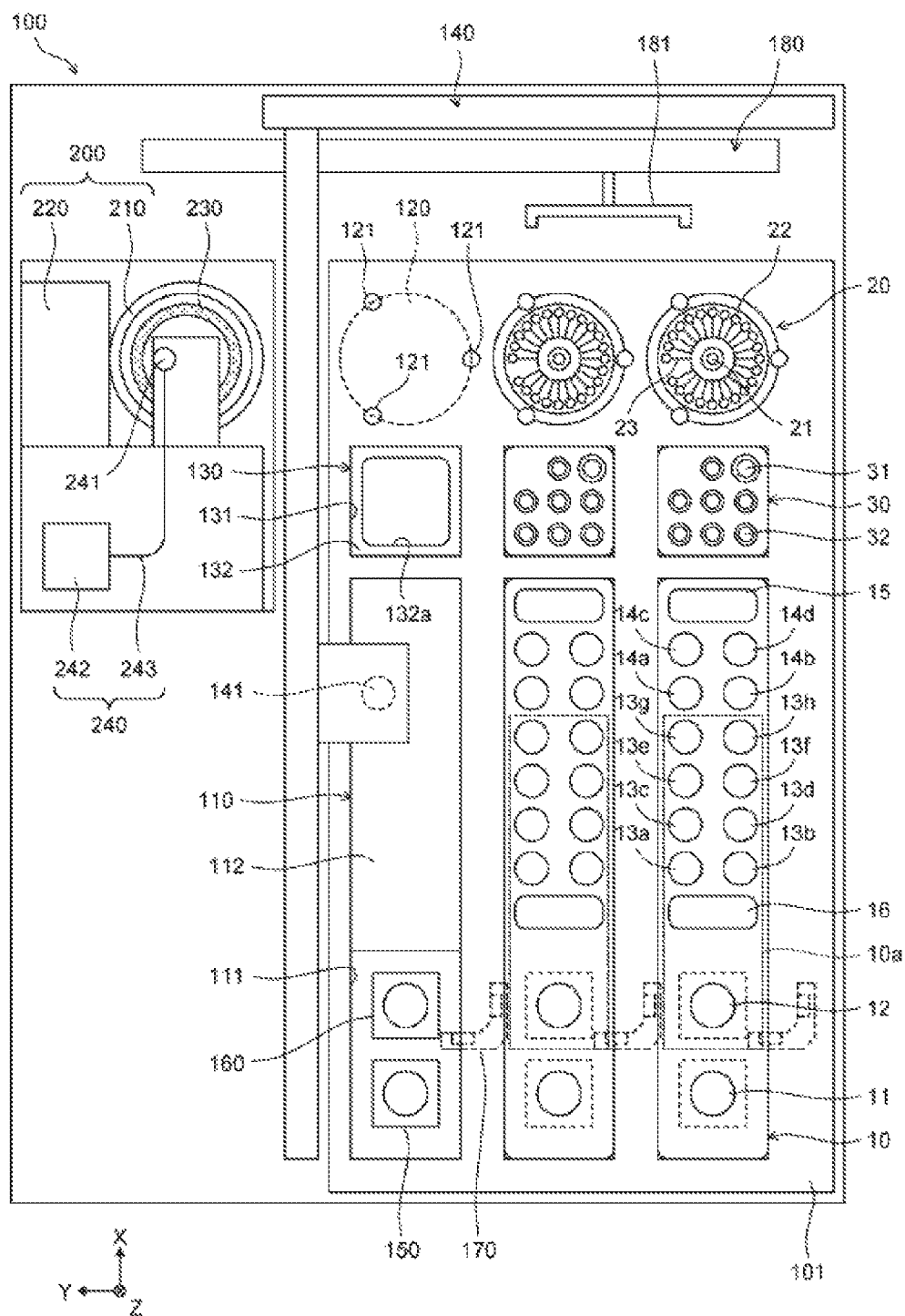
FIG. 1 is a view, as seen from the upper side, schematically illustrating a configuration of a nucleic acid analyzer according to an embodiment 1.

Embodiments are explained with referring to drawings. In the respective drawings referenced herein, the same constitutions are designated by the same reference numerals and duplicate explanation concerning the same constitutions is basically omitted. All of the drawings are provided to illustrate the respective examples only. No dimensional proportions in the drawings shall impose a restriction on the embodiments. For this reason, specific dimensions and the like should be interpreted with the following descriptions taken into consideration. In addition, the drawings include parts whose dimensional relationship and ratio are different from one drawing to another.

Embodiment 1

In an embodiment 1, the disclosure is applied to a device that automatically performs nucleic acid extraction, Real-Time PCR, detection of a nucleic acid amplification reaction, and nucleic acid analysis.

As illustrated in FIG. 1, a nucleic acid analyzer 100 includes a plate member 101, a dispensing unit 140, temperature adjustment parts 150, 160, a magnetic force application part 170, a transport unit 180, a rotation part 200, a first temperature adjustment part 230, and a detector 240. In FIG. 1, the X, Y, Z axes are orthogonal to each other. The positive X-axis direction indicates the backward, the positive Y-axis direction indicates the leftward, and the positive Z-axis direction indicates the vertical downward. In the following drawings, the X, Y, Z axes are also the same as the X, Y, Z axes illustrated in FIG. 1. The X-axis corresponds to a first axis, and the Y-axis corresponds to a second axis. Although the X-axis and the Y-axis orthogonally intersect in an embodiment 1, the X-axis and the Y-axis do not need to intersect completely orthogonally.

The plate member 101 is parallel to the XY-plane. The plate member 101 includes three first container setting parts 110, three second container setting parts 120, and three third container setting parts 130. The plate member 101 includes three rows, in each of which one first container setting part 110, one second container setting part 120, and one third container setting part 130 are arranged along the X-axis in a plan view. In other words, in a plan view, the three first container setting parts 110 are disposed along the Y-axis, the three second container setting parts 120 are disposed along the Y-axis, and the three third container setting parts 130 are disposed along the Y-axis.

Figure 2A:
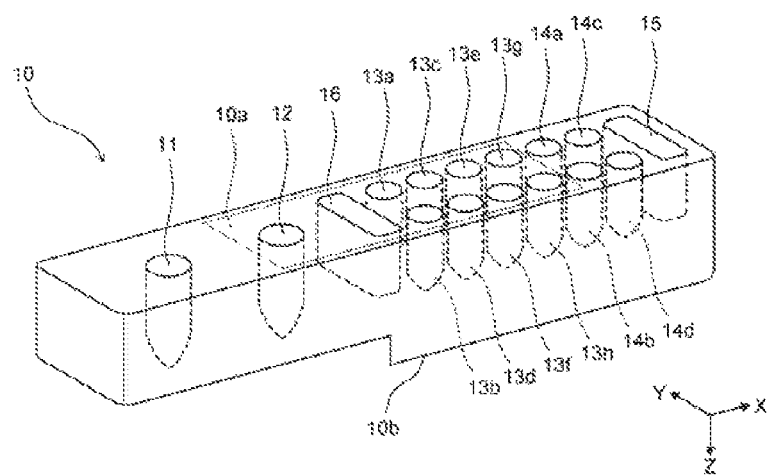
FIG. 2A is a perspective view schematically illustrating a configuration of a first container according to an embodiment 1.

Each first container setting part 110 is a setting part for setting a first container 10. The first container setting part 110 includes an opening 111 formed in the plate member 101, and a support plate 112 on the vertically lower side of the plate member 101. In a plan view, the opening 111 has a slightly larger contour than the outline of the first container 10, and the support plate 112 is provided on the back side of the opening 111. A lower end 10b of the first container 10 illustrated in FIG. 2A is supported vertically upward by the support plate 112, and the lateral surfaces of the first container 10 are supported by the opening 111, thus the first container 10 is set in the first container setting part 110. When analysis of nucleic acids is started, the first container 10 is set in the first container setting part 110. The first container 10 set in the first container setting part 110 has a shape long in the X-axis direction.

As illustrated in FIGS. 1 and 2A, the first container 10 includes a reaction part 11, a reagent storage 12, reagent storages 13a to 13h, mixing parts 14a to 14d, a reagent storage 15, and a waste fluid storage 16. The reaction part 11, the reagent storage 12, the reagent storages 13a to 13h, the mixing parts 14a to 14d, the reagent storage 15, and the waste fluid storage 16 are provided in the first container 10 to be open upward, and each a well which can store liquid. The reagent storages 12, 13a to 13h pre-store reagents for nucleic acid extraction. The top of the reagent storage 12, the reagent storages 13a to 13h, and the waste fluid storage 16 is sealed by an aluminum seal 10a. When the first container 10 is set in the first container setting part 110, reagents are stored in the reagent storage 15.

Specifically, the reagent storage 12 pre-stores a reagent containing magnetic particles and magnetic particle preservation solution. The reagent storages 13a to 13h respectively pre-stores solubilized solution, proteinase K, oil, eluate, undiluted solution of reagent for extraction, undiluted second cleaning solution, undiluted solution of diluent, and undiluted first cleaning solution. Extraction of nucleic acids using the first container 10 is described with reference to FIG. 13 later.

The first container 10 is set in the first container setting part 110 so that the reagent storages of the first container 10 are disposed along the X-axis. When the first container 10 is set in the first container setting part 110, the reaction part 11 and the reagent storage 12 are also disposed along the X-axis.

As illustrated in FIG. 1, the second container setting part 120 is a setting part for setting a second container 20 as a reaction container. Each of the three second container setting parts 120 is disposed on the positive X-axis direction side of a corresponding one of the three first container setting parts 110. Thus, the second container setting part 120 is disposed on the positive X-axis direction side of the first container 10 set in the first container setting part 110. The second container setting part 120 includes the upper surface of the plate member 101, and three pins 121 set on the upper surface of the plate member 101. The later-described engaged sections 27a of the second container 20 are engaged with the three pins 121, and thus the second container 20 is set in the second container setting part 120. The second container setting parts 120 are disposed so that injection ports 21 of the second containers 20 disposed in the respective three second container setting parts 120 are arranged along the Y-axis.

Each second container 20 includes the injection port 21, twenty-three storages 22, and twenty-three flow paths 23 that connect the injection port 21 and the twenty-three storages 22. The second container 20 is a disk-shaped container in which the injection port 21 is disposed at the center position, and the twenty-three storages 22 are disposed at positions on the outer circumferential side with a constant radius from the center position with regular intervals in a circumferential direction. As described later, the center position of the second container 20 is the rotation center when the second container 20 is rotated. That is, the twenty-three storages 22 are disposed side by side in the circumferential direction at positions with a constant radius from the rotation center of the second container 20. It is to be noted that although the second container 20 is a disk-shaped container in an embodiment 1, the second container 20 is not necessarily a disk-shaped container.

Figure 2B:
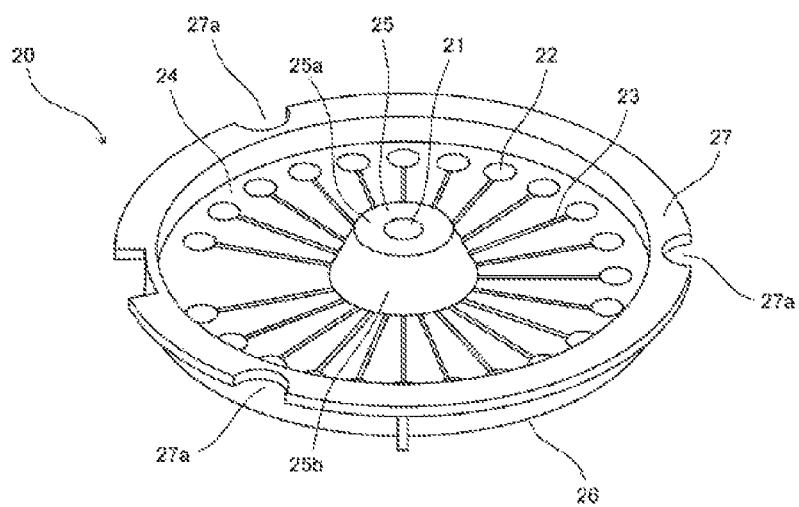
FIG. 2B is a perspective view schematically illustrating a configuration of a second container according to an embodiment 1.

As illustrated in FIG. 2B, specifically, the second container 20 includes an upper surface section 24, a projection 25, a lower surface section 26, and a flange section 27. The projection 25 is disposed at the center position of the second container 20. The projection 25 has a reduced thickness in the vertical direction at closer to the end of the second container 20, and is axial symmetry with respect to a central axis of a line which is through the center position of the second container 20 and parallel to the vertical direction. The projection 25 includes an upper surface section 25a and an inclined surface section 25b. The upper surface of the upper surface section 25a is parallel to a horizontal plane.

The injection port 21 is formed in the upper surface section 25a, and is a hole parallel to the vertical direction.

The upper surface section 24 is made of a member having translucency. The upper surface of the upper surface section 24 is a surface parallel to the horizontal plane, and the lower surface of the upper surface section 24 includes a depressed section and a groove for forming the storages 22 and the flow paths 23. The storages 22 and the flow paths 23 are formed by attaching thin film-shaped ABS resin to the lower surface of the upper surface section 24. The lower surface section 26 is made of thin film-shaped aluminum having a high thermal conductivity. The lower surface section 26 is attached from the lower side with respect to the ABS resin attached to the lower surface of the upper surface section 24.

The flange section 27 is a flat plate parallel to the horizontal plane formed on the outer side of the upper surface section 24. In the flange section 27, three engaged sections 27a are formed. Each engaged section 27a is a notch. The engaged section 27a is engaged with the later-described engagement section 214 of the container setting part 210. The engaged section 27a only has to be engaged with the engagement section 214 of the container setting part 210, and may be a hole, a depressed section, or a projection instead of a notch.

Extraction liquid is injected into the injection port 21, the extraction liquid containing the nucleic acids extracted in the first container 10 positioned on the negative X-axis side. The storage 22 pre-stores reagents for amplifying the nucleic acids in the extraction liquid. The second container 20 is a reaction vessel to cause reaction between the extraction liquid injected from the injection port 21 and the reagents in the storages 22.

In an embodiment 1, the second container 20 for amplifying nucleic acids includes the storages 22. Thus, analysis can be concurrently performed for as many as the number of storages 22 on the nucleic acids extracted in the first container 10 disposed on the negative X-axis direction side. Therefore, the efficiency of analysis can be improved. For instance, when the second container 20 includes one storage, multiple second containers 20 need to be set for extracted nucleic acids to conduct analysis multiple times. However, according to an embodiment 1, analysis can be concurrently conducted multiple times for extracted nucleic acids by setting one second container 20. Therefore, the installation area of the nucleic acid analyzer 100 can be reduced.

The injection port 21 of the second container 20 set in the second container setting part 120 is positioned at substantially the center of the width of the first container 10 in the Y-axis direction, in the Y-axis direction in a plan view. Consequently, the first container 10 and the second container 20 are compactly disposed, and the installation area of the nucleic acid analyzer 100 can be reduced.

Figure 3A:
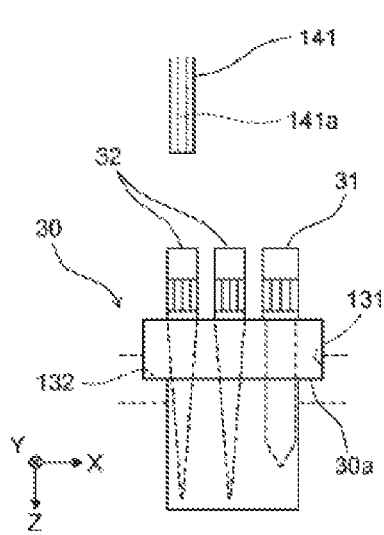
FIGS. 3A and 3B are side views schematically illustrating a configuration of a third container and an aspiration part according to an embodiment 1.

As illustrated in FIG. 1, each third container setting part 130 is a setting part for setting the third container 30. The third container setting part 130 includes an opening 131 formed in the plate member 101, and a support plate 132 on the vertically lower side of the plate member 101. In a plan view, the opening 131 has a slightly larger contour than the outline of the third container 30. An opening 132a is formed in the support plate 132. The trunk section of the third container 30 is inserted through the opening 132a, and a lower surface 30a of a flange section formed on the outer circumference of the third container 30 illustrated in FIG. 3A is supported vertically upward by the support plate 132, and thus the third container 30 is set in the third container setting part 130. When analysis of nucleic acids is started, the third container 30 is set in the third container setting part 130.

Figure 3B:
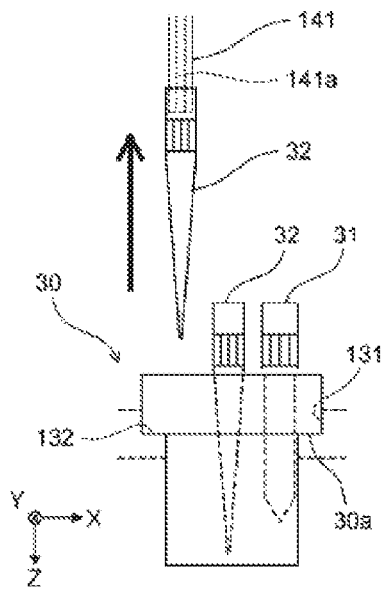

As illustrated in FIGS. 1 and 3A, the third container 30 holds one piercing tip 31, and seven pipette tips 32. The piercing tip 31 is a tip for piercing the aluminum seal 10a of the first container 10 to open the top of a storage on the lower side of the aluminum seal 10a. Each pipette tip 32 has a hole penetrating in the vertical direction. As illustrated in FIGS. 3A and 3B, when an aspiration part 141 of the dispensing unit 140 is lowered from right above the pipette tip 32, the pipette tip 32 is mounted on the lower end of the aspiration part 141. The aspiration part 141 is raised, and thus the pipette tip 32 is removed from the third container 30. Similarly, the piercing tip 31 is mounted on the lower end of the aspiration part 141. A hole 141a is formed in the aspiration part 141 so that liquid can be aspirated or discharged through the lower end of the aspiration part 141.

Figure 3C:
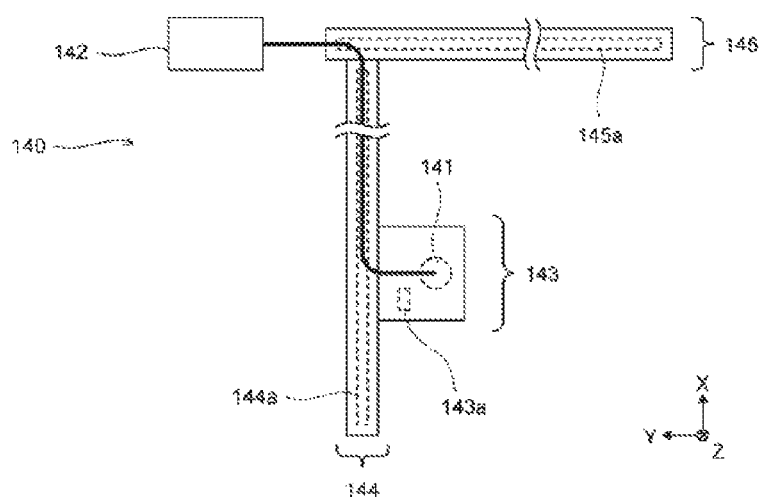
FIG. 3C is a view schematically illustrating a configuration of a dispensing unit according to an embodiment 1.

Returning to FIG. 1, the dispensing unit 140 transports the extraction liquid stored in the first container 10 to the injection port 21 of the second container 20 from the first container 10. As illustrated in FIG. 3C, the dispensing unit 140 includes the aspiration part 141, a pump 142, a vertical transport part 143, a forward-backward transport part 144, and a horizontal transport part 145. The piercing tip 31 and the pipette tips 32 are detachably attachable to the aspiration part 141. The aspiration part 141 includes a nozzle. The pump 142 is connected to the hole 141a of the aspiration part 141. The pump 142 applies a positive pressure or a negative pressure to the aspiration part 141 to cause liquid to be aspirated or discharged through the pipette tip 32 mounted on the lower end of the aspiration part 141.

The vertical transport part 143 includes a rail 143a which extends along the Z-axis, and a stepping motor which is not illustrated. The vertical transport part 143 drives the stepping motor to transport the aspiration part 141 along the rail 143a in the Z-axis direction. The forward-backward transport part 144 includes a rail 144a which extends along the X-axis, and a stepping motor which is not illustrated. The rail 144a is a rail for moving the aspiration part 141 along the X-axis. The forward-backward transport part 144 drives the stepping motor to transport the vertical transport part 143 along the rail 144a in the X-axis direction. The horizontal transport part 145 includes a rail 145a which extends along the Y-axis, and a stepping motor which is not illustrated. The rail 145a is a rail for moving the aspiration part 141 along the Y-axis. The horizontal transport part 145 drives the stepping motor to transport the forward-backward transport part 144 along the rail 145a in the Y-axis direction.

Movement of the aspiration part 141 is made possible along the X, Y, Z axes inside the nucleic acid analyzer 100 by the vertical transport part 143, the forward-backward transport part 144, and the horizontal transport part 145. The dispensing unit 140 transports extraction liquid from the first container 10 to the second container 20 along the X-axis. Specifically, the dispensing unit 140 aspirates extraction liquid from the first container 10 by the pipette tip 32 mounted on the aspiration part 141. Subsequently, the dispensing unit 140 moves the pipette tip 32 to the injection port 21 of the second container 20 disposed on the positive X-axis direction side of the first container 10 from which the extraction liquid is aspirated. The dispensing unit 140 then discharges the extraction liquid to the second container 20 through the injection port 21.

As illustrated in FIG. 1, the first container 10 includes two rows of reagent storages arranged along the X-axis, the two rows being in the Y-axis direction in a plan view. Specifically, the first container 10 includes a row of reagent storages 13a, 13c, 13e, 13g, and a row of reagent storages 13b, 13d, 13f, 13h. The dispensing unit 140 moves the pipette tip 32 in the X-axis direction and the Y-axis direction to aspirate the reagents from the reagent storages 13a to 13h. Consequently, the length of the first container 10 in the X-axis direction can be reduced, as compared with the case where all the reagent storages are arranged in the X-axis direction in the first container 10. Thus, the layout in the nucleic acid analyzer 100 can be formed compactly.

The dispensing unit 140 dispenses reagents in the first container 10 set in each first container setting part 110 through a dispensing path set for each of the three first container setting part 110. Thus, one dispensing unit 140 performs a dispensing operation on the three first container setting parts 110. Similarly, one dispensing unit 140 performs a dispensing operation on the three second container setting parts 120. When one common dispensing unit 140 is used for the containers like this, the layout in the nucleic acid analyzer 100 can be formed compactly, as compared with the case where multiple dispensing units are used.

Figure 4A:
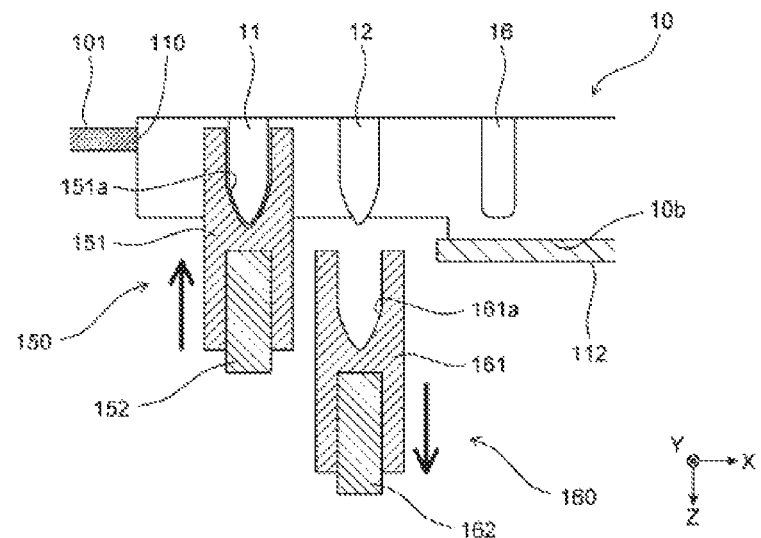
FIG. 4A is a cross-sectional view schematically illustrating a configuration of a temperature adjustment part disposed below a first container setting part according to an embodiment 1.

As illustrated in FIG. 1, the temperature adjustment parts 150, 160 are disposed at a frontward position in the opening 111 of the first container setting part 110 in a plan view. As illustrated in FIG. 4A, the temperature adjustment part 150 includes a heat block 151 and a heater 152, and heats the reaction part 11 of the first container 10 set in the first container setting part 110. A hole 151a having substantially the same shape as the reaction part 11 is formed in the heat block 151. When the reaction part 11 is heated, the temperature adjustment part 150 is moved upward, and the reaction part 11 is stored in the hole 151a. In this state, heat of the heater 152 is transmitted to the reaction part 11 through the heat block 151. When heating of the reaction part 11 is completed, the temperature adjustment part 150 is moved downward.

Similarly, the temperature adjustment part 160 includes a heat block 161 and a heater 162, and heats the reagent storage 12 of the first container 10 set in the first container setting part 110. When the reagent storage 12 is heated, the temperature adjustment part 160 is moved upward, and the reagent storage 12 is stored in a hole 161a. In this state, heat of the heater 162 is transmitted to the reagent storage 12 through the heat block 161. When heating of the reagent storage 12 is completed, the temperature adjustment part 160 is moved downward.

Figure 4B:
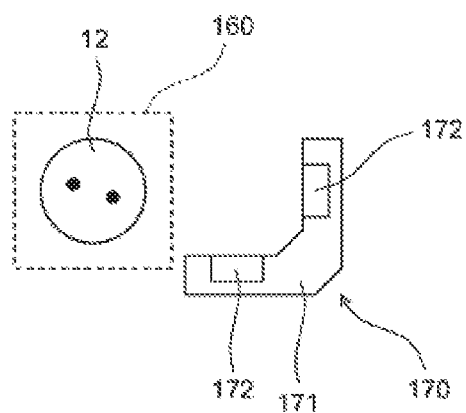
FIGS. 4B and 4C are views schematically illustrating a configuration of a magnetic force application part according to an embodiment 1.
Figure 4C:
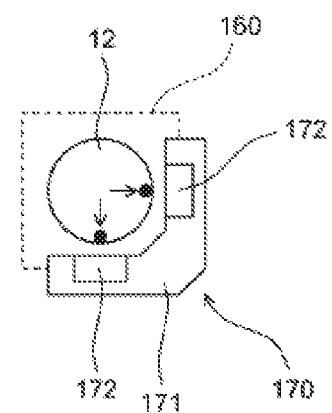

As illustrated in FIG. 1, the magnetic force application part 170 is disposed on the vertically lower side of the plate member 101, and is configured to be movable in the Y-axis direction. As illustrated in FIGS. 4B and 4C, the magnetic force application part 170 includes a support section 171 and two magnets 172. When the magnetic force application part 170 is used, as illustrated in FIG. 4A, the temperature adjustment part 160 is retracted vertically downward. As illustrated in FIG. 4C, the magnetic force application part 170 is then brought close to the reagent storage 12 of the first container 10 set in the first container setting part 110. Consequently, the magnetic particles contained in the reagent storage 12 as illustrated in FIG. 4B are attracted to the magnet 172, and adhere to the wall surface of the reagent storage 12 on the negative X-axis side, and the wall surface of the reagent storage 12 on the negative Y-axis side as illustrated in FIG. 4C.

As illustrated in FIG. 1, the transport unit 180 includes a hand section 181, and a mechanism for moving the hand section 181 in the Y-axis direction. The transport unit 180 grasps and transports the second container 20 between the positions of the second container setting part 120 and the rotation part 200. The transport unit 180 transports the second container 20 to the position of the rotation part 200, the second container 20 containing injected extraction liquid and set in the second container setting part 120. Instead of grasping and transporting the second container 20 by the hand section 181, the transport unit 180 may attract and transport the upper surface of the upper surface section 24 of the second container 20 with an attracting part.

The rotation part 200 includes the container setting part 210 and a rotation drive part 220. The container setting part 210 is configured to provide and attach the reaction container 20. The rotation part 200 rotates the second container 20 into which extraction liquid has been injected to deliver and supply the extraction liquid to the storage 22 by a centrifugal force through the flow path 23. Specifically, the rotation drive part 220 rotates the container setting part 210 in which the second container 20 is set by applying a driving force to the later-described first outer-side surface 212 of the container setting part 210. The rotation drive part 220 rotates the container setting part 210 to rotate the second container 20, to supply the extraction liquid injected into the injection port 21 to the storage 22 by a centrifugal force through the flow path 23. The first temperature adjustment part 230 adjusts the temperature of the second container 20 which is rotated by the rotation part 200 and set in the container setting part 210, so that a nucleic acid amplification reaction occurs in the storage 22. The first temperature adjustment part 230 includes a Peltier device.

At this point, in the storage 22, the nucleic acids contained in the extraction liquid are mixed with the reagents pre-stored in the storage 22. The storage 22 pre-stores reagents for amplifying detection target nucleic acid for which mutation has occurred in a detection target region of nucleic acids, and reagents containing fluorescent probes that bind to detection target nucleic acid. The fluorescent probes contain fluorescent substances. When the fluorescent probes bind to the detection target nucleic acid, the detection target nucleic acid is labeled with the fluorescent substances. When the fluorescent probes bind to the detection target nucleic acid, irradiation of the fluorescent substances of the fluorescent probes with excitation light causes fluorescence to be generated from the fluorescent substances. On the other hand, when the fluorescent probes do not bind to the detection target nucleic acid, irradiation of the fluorescent substances of the fluorescent probes with excitation light does not cause fluorescence to be generated from the fluorescent substances.

Adjustment of the temperature by the first temperature adjustment part 230 causes a nucleic acid amplification reaction to occur in the storage 22. When the detection target nucleic acid is contained in the nucleic acids, the detection target nucleic acid is amplified in the storage 22, whereas when the detection target nucleic acid is not contained in the nucleic acids, the detection target nucleic acid is not amplified in the storage 22. Therefore, when the detection target nucleic acid is amplified, the amplified detection target nucleic acid is labeled with the fluorescent substances of the fluorescent probes, thus when the storage 22 is irradiated with excitation light, fluorescence is generated according to the amount of amplification.

The rotation part 200 sequentially transports each storage 22 with a temperature adjusted so that the storage 22 is positioned at the detection position of the detector 240. Specifically, the rotation drive part 220 rotates the container setting part 210, and sequentially positions the storage 22 of the second container 20 set in the container setting part 210 to a detection position in accordance with a predetermined order.

The detector 240 detects a nucleic acid amplification reaction which occurs in the storage 22 positioned at the detection position by the rotation part 200. Specifically, the detector 240 detects the intensity of a fluorescent signal which indicates the amount of amplified product due to a nucleic acid amplification reaction.

Figure 5:
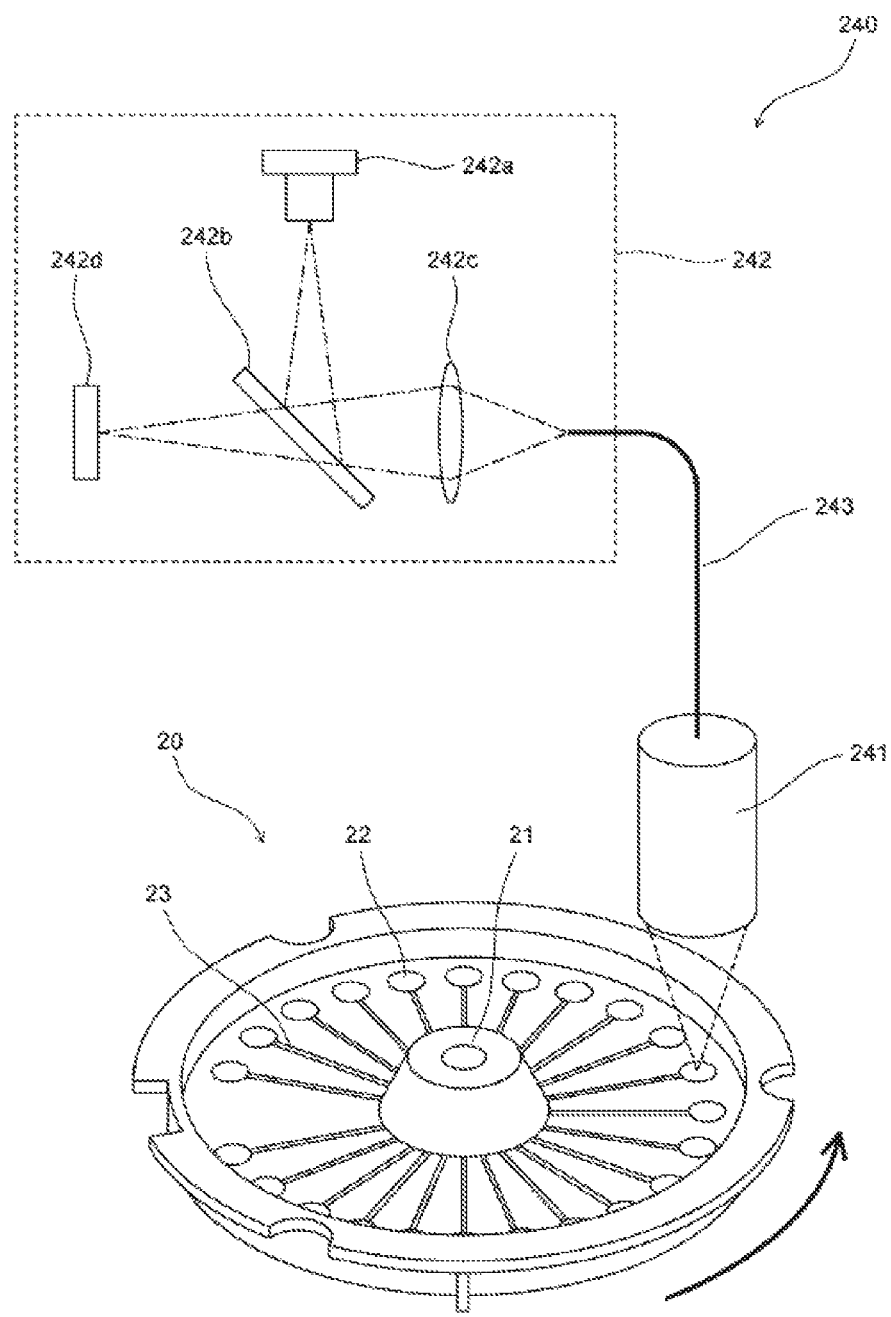
FIG. 5 is a view schematically illustrating a configuration of a detector according to an embodiment 1.

As illustrated in FIGS. 1 and 5, the detector 240 includes a detection head 241, and an optical unit 242 coupled to the detection head 241 via an optical fiber 243. The detector 240 detects a nucleic acid amplification reaction by irradiating the storage 22 of the second container 20 with light. The detection head 241 is disposed so as to irradiate the storage 22 with light and face the storage 22 of the second container 20. The optical unit 242 includes a light source 242a, a dichroic mirror 242b, a condenser lens 242c, and a light detector 242d.

The light source 242a emits excitation light with a predetermined wavelength. When fluorescent probes bind to a detection target substance, excitation light emitted from the light source 242a excites the fluorescent substance of the fluorescent probes to generate fluorescence. The dichroic mirror 242b reflects the excitation light emitted from the light source 242a, and transmits the fluorescence generated from the fluorescent substance of the fluorescent probes. The condenser lens 242c collects the excitation light reflected by the dichroic mirror 242b, and guides the light to the optical fiber 243. In addition, the condenser lens 242c collects the fluorescence emitted from the optical fiber 243 to the condenser lens 242c, and guides the light to the dichroic mirror 242b. The light detector 242d receives the fluorescence passing through the dichroic mirror 242b, measures the intensity of the received fluorescence, and outputs an electrical signal according to the intensity of the fluorescence.

Thus, the later-described analysis part 401 generates pieces of time series data from an electrical signal of fluorescence detected by the light detector 242d of the detector 240, the pieces of time series data indicating a nucleic acid amplification reaction which occurs in each storage 22. The analysis part 401 then determines based on the time series data whether or not a detection target substance is contained in each storage 22, and displays a result of the determination, and the like, on the later-described display part 403. Now, analysis of nucleic acids is completed.

Here, as illustrated in FIG. 1, the rotation part 200, the first temperature adjustment part 230, and the detector 240 are disposed at the same position in a plan view. That is, when seen from the upper side, part of the rotation part 200, part of the first temperature adjustment part 230, and part of the detector 240 overlap each other. When the rotation part 200, the first temperature adjustment part 230, and the detector 240 are disposed at the same position in a plan view like this, temperature control and detection for the second container 20 can be smoothly performed, thus Real-Time PCR can be performed for each storage 22 of the second container 20. Also, the rotation part 200, the first temperature adjustment part 230, and the detector 240, can be compactly disposed in the nucleic acid analyzer 100.

The rotation part 200, the first temperature adjustment part 230, and the detector 240 are at positions different from any position on the line that connects the first container setting part 110 and the second container setting part 120. Also, the transport unit 180 transports the second container 20 set in the second container setting part 120 to the positions of the rotation part 200, the first temperature adjustment part 230, and the detector 240. Thus, when the dispensing unit 140 moves on the line that connects the first container setting part 110 and the second container setting part 120, the movement path of the dispensing unit 140 does not overlap with the positions of the rotation part 200, the first temperature adjustment part 230, and the detector 240, thus the dispensing unit 140 can be smoothly driven.

The rotation drive part 220 rotates the container setting part 210 by applying a driving force to the first outer-side surface 212 of the container setting part 210 in which the second container 20 is set. The detector 240 is disposed on the upper side of the second container 20 set in the container setting part 210, and the first temperature adjustment part 230 is disposed on the lower side of the second container 20 set in the container setting part 210. Consequently, PCR reaction can be detected in real time with a simple configuration while performing temperature control with high accuracy.

It is to be noted that the first temperature adjustment part 230 and the detector 240 may be disposed at positions located above and below the second container 20 set in the container setting part 210. The detector 240 may detect a nucleic acid amplification reaction which occurs in the storages 22 with the second container 20 set in the container setting part 210 interposed between the first temperature adjustment part 230 and the detector 240 in the vertical direction. For instance, the detector 240 may be disposed on the lower side of the second container 20 set in the container setting part 210, and the first temperature adjustment part 230 may be disposed on the upper side of the second container 20 set in the container setting part 210.

Figure 6:
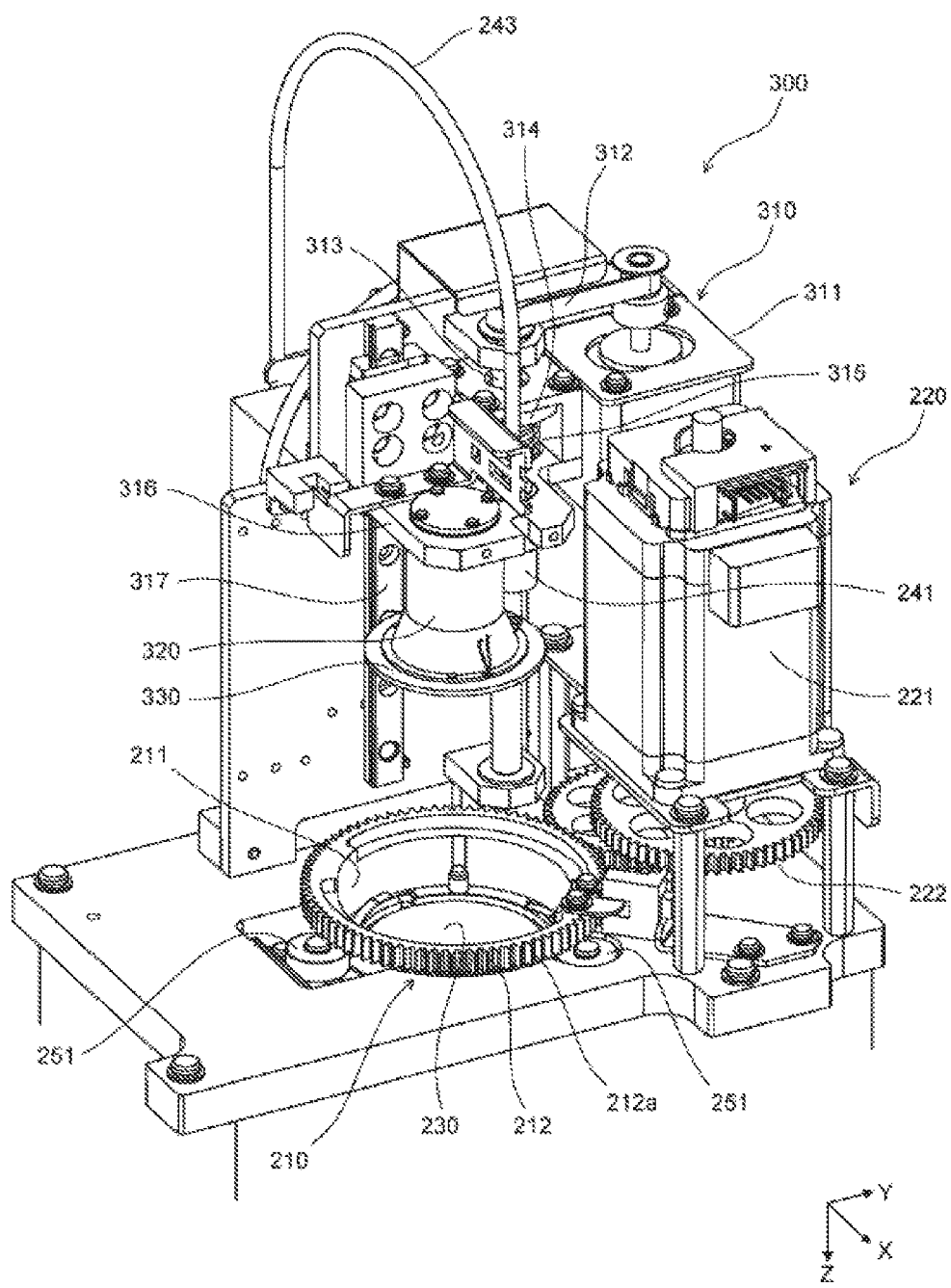
FIG. 6 is a perspective view illustrating a configuration of a rotation part, a detector, and an urging part according to an embodiment 1.
Figure 7A:
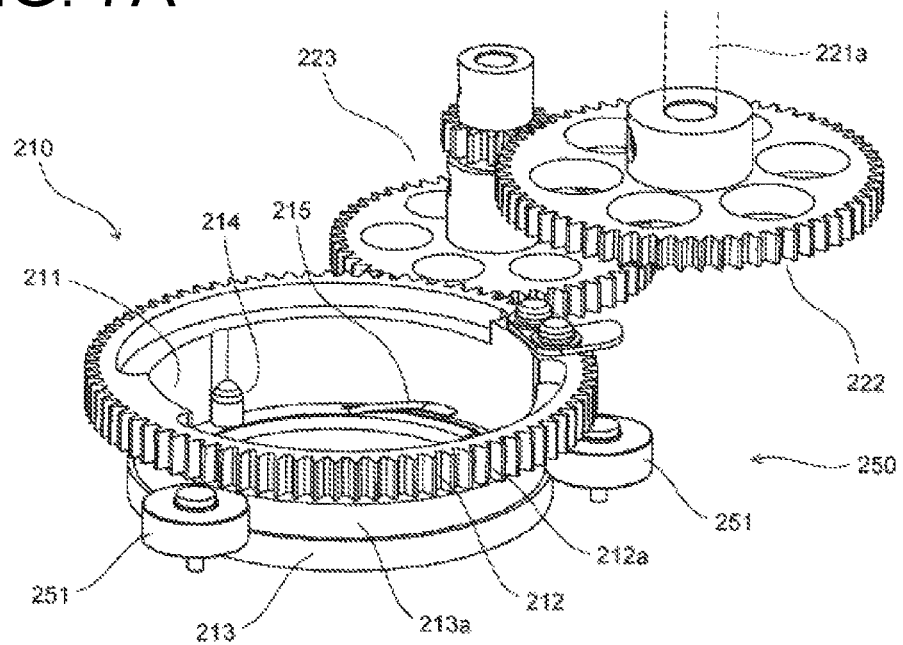
FIG. 7A is a perspective view illustrating a configuration of a container setting part, a rotation drive part, and a guide part according to an embodiment 1.
Figure 7B:
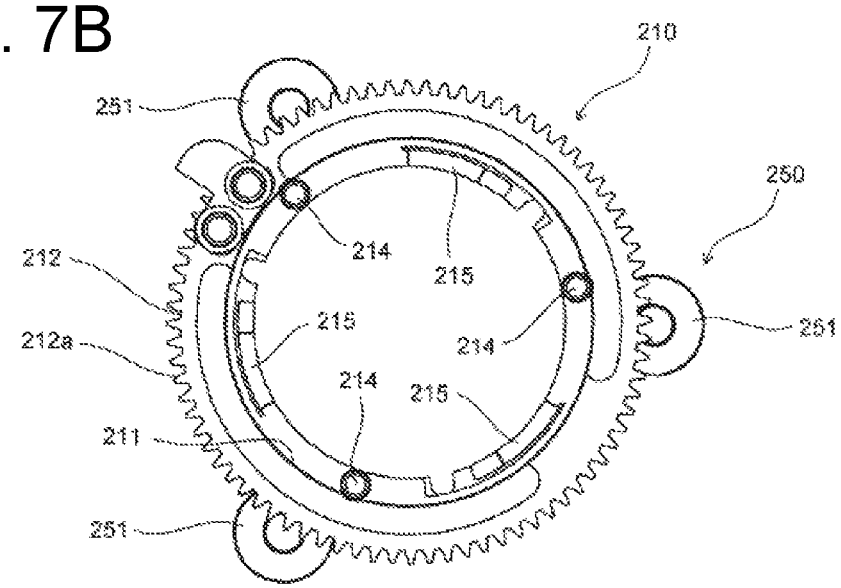
FIG. 7B is a plan view illustrating a configuration of a container setting part and a guide part according to an embodiment 1.

As illustrated in FIGS. 6, 7A, and 7B, the container setting part 210 includes an inner-side surface 211, a first outer-side surface 212, a second outer-side surface 213, three engagement sections 214, and three elastic members 215. The shape of the container setting part 210 is a cylindrical shape having openings at the top and bottom. It is to be noted that the container setting part 210 may not be necessarily a cylindrical shape. The container setting part 210 may be such that the later-described first outer-side surface 212 and groove 213a are cylindrical, and the other portions are angulated. Also, the shape of the container setting part 210 may not necessarily have openings at the top and bottom. For instance, the container setting part 210 may include a bottom surface having a high thermal conductivity. In this case, the temperature of the lower surface of the lower surface section 26 of the second container 20 may be adjusted by the first temperature adjustment part 230 via the bottom surface of the container setting part 210.

The inner-side surface 211, the first outer-side surface 212, and the second outer-side surface 213 are cylindrical. Gear sections 212a are formed on the first outer-side surface 212. In the second outer-side surface 213, a groove 213a with a constant width in the vertical direction is formed over the entire circumference of the second outer-side surface 213. Also, the nucleic acid analyzer 100 includes a guide part 250 that is configured to come into contact with the second outer-side surface 213 and is configured to guide and support the container setting part 210 in rotation. The guide part 250 includes three guide members 251 that are provided and fitted in the groove 213a of the second outer-side surface 213. Each guide member 251 includes a roller. Fitting of the guide members 251 to the groove 213a causes the container setting part 210 to be rotatable with a fixed position in a horizontal plane and a fixed position in the vertical direction.

It is to be noted that instead of the groove 213a, projections with a constant width in the vertical direction may be formed on the second outer-side surface 213, over the entire circumference of the second outer-side surface 213. In this case, for instance, multiple pairs of two rollers, between which the top and bottom of the projections of the second outer-side surface 213 are interposed, may be disposed on the outer circumference of the second outer-side surface 213.

As illustrated in FIGS. 7A and 7B, the inner-side surface 211 defines a cylindrical space. In a lower portion of the cylindrical space surrounded by the inner-side surface 211 of the container setting part 210, a rack parallel to a horizontal plane is provided over the entire circumference of the inner-side surface 211. The engagement sections 214 and the elastic members 215 are also disposed at the rack in the cylindrical space surrounded by the inner-side surface 211. Each engagement section 214 has a cylindrical shape with a diameter slightly smaller than the diameter of each engaged section 27a of the second container 20. Each elastic member 215 includes a spring such as a plate spring. The second container 20 is inserted into the cylindrical space, and is provided in the container setting part 210. Specifically, each engagement section 214 is engaged with the engaged section 27a of the second container 20, and the elastic members 215 support the lower surface of the flange section 27 of the second container 20, thereby setting the second container 20 in the container setting part 210.

As illustrated in FIGS. 6 and 7A, the rotation drive part 220 includes a motor 221 and transmission gears 222, 223. In addition, the rotation drive part 220 includes the gear sections 212a as a component, the gear sections 212a being formed in the first outer-side surface 212 of the container setting part 210. The motor 221 is a stepping motor. As illustrated in FIG. 7A, the transmission gears 222, 223 couple a drive shaft 221a of the motor 221 to the gear sections 212a of the first outer-side surface 212. Specifically, the center of the transmission gear 222 is connected to the drive shaft 221a of the motor 221. The transmission gear 222 is engaged with an upper gear section of the transmission gear 223. The gear section 212a of the first outer-side surface 212 is engaged with a lower gear section of the transmission gear 223. The diameter of the upper gear section of the transmission gear 223 is smaller than the diameter of the lower gear section of the transmission gear 223.

In this manner, when the rotation of the drive shaft 221a is transmitted to the gear sections 212a, the transmission gear 223 functions as an acceleration gear, and thus the rotational speed of the container setting part 210 can be increased higher than the rotational speed of the drive shaft 221a.

It is to be noted that as a unit to transmit a driving force of the motor 221 to the container setting part 210, a belt wrapped around the outer circumference of the drive shaft 221a and the outer circumference of the first outer-side surface 212 may be used. When a belt is used, if a frictional force between the belt, and the drive shaft and the first outer-side surface 212 is small, the belt slips, thus the drive shaft 221a and the first outer-side surface 212 need to be spaced apart. However, in this case, the installation area of the nucleic acid analyzer 100 is increased. Therefore, as described above, it is desirable that the driving force of the motor 221 be transmitted to the container setting part 210 by the transmission gears 222, 223 and the gear section 212a.

As illustrated in FIG. 6, the nucleic acid analyzer 100 includes an urging part 300 at the positions of the rotation part 200, the first temperature adjustment part 230, and the detector 240. The urging part 300 is disposed on the side of the second container 20 set in the container setting part 210 opposite to the first temperature adjustment part 230. Specifically, the urging part 300 is disposed above the second container 20 set in the container setting part 210. Also, the urging part 300 is configured to urge the second container 20 set in the container setting part 210 toward the first temperature adjustment part 230.

The urging part 300 includes a movement mechanism 310, a supporting body 320, and a holding member 330. The movement mechanism 310 includes a motor 311, a belt 312, a gear 313, a support section 314, a spring 315, a support member 316, and a rail 317. The motor 311 is a stepping motor. The belt 312 connects the drive shaft of the motor 311 and the gear 313. The gear 313 is rotatably provided in a member in the nucleic acid analyzer 100. The support section 314 is provided in the gear 313 so as to be vertically moved according to the rotation of the gear 313. The upper end of the spring 315 is provided at the lower surface of support section 314, and the lower end of the spring 315 is provided at the upper surface of the support member 316. The support member 316 is provided in the rail 317 so as to be movable along the rail 317. The rail 317 is provided in a member in the nucleic acid analyzer 100, and extends in the vertical direction.

The supporting body 320 is provided at the lower surface of the support member 316. The holding member 330 is provided at the lower end of the supporting body 320. When the drive shaft of the motor 311 rotates, the gear 313 is rotated, and the support section 314 is moved vertically. When the support section 314 is moved vertically, the support member 316, the supporting body 320, and the holding member 330 are moved vertically via the spring 315 according to the movement of the support section 314. Thus, the holding member 330 can hold the side of the second container 20 set in the container setting part 210 opposite to the first temperature adjustment part 230. Specifically, the holding member 330 can hold the upper surface of the upper surface section 24 of the second container 20 set in the container setting part 210.

Between the detection head 241 and the optical unit 242 of the detector 240, the detection head 241 is disposed on the side of the second container 20 set in the container setting part 210 opposite to the first temperature adjustment part 230. The detection head 241 is supported by the support member 316 that supports the holding member 330 and vertically moves. It is to be noted that the entire detector 240 may be supported by the support member 316.

Figure 8:
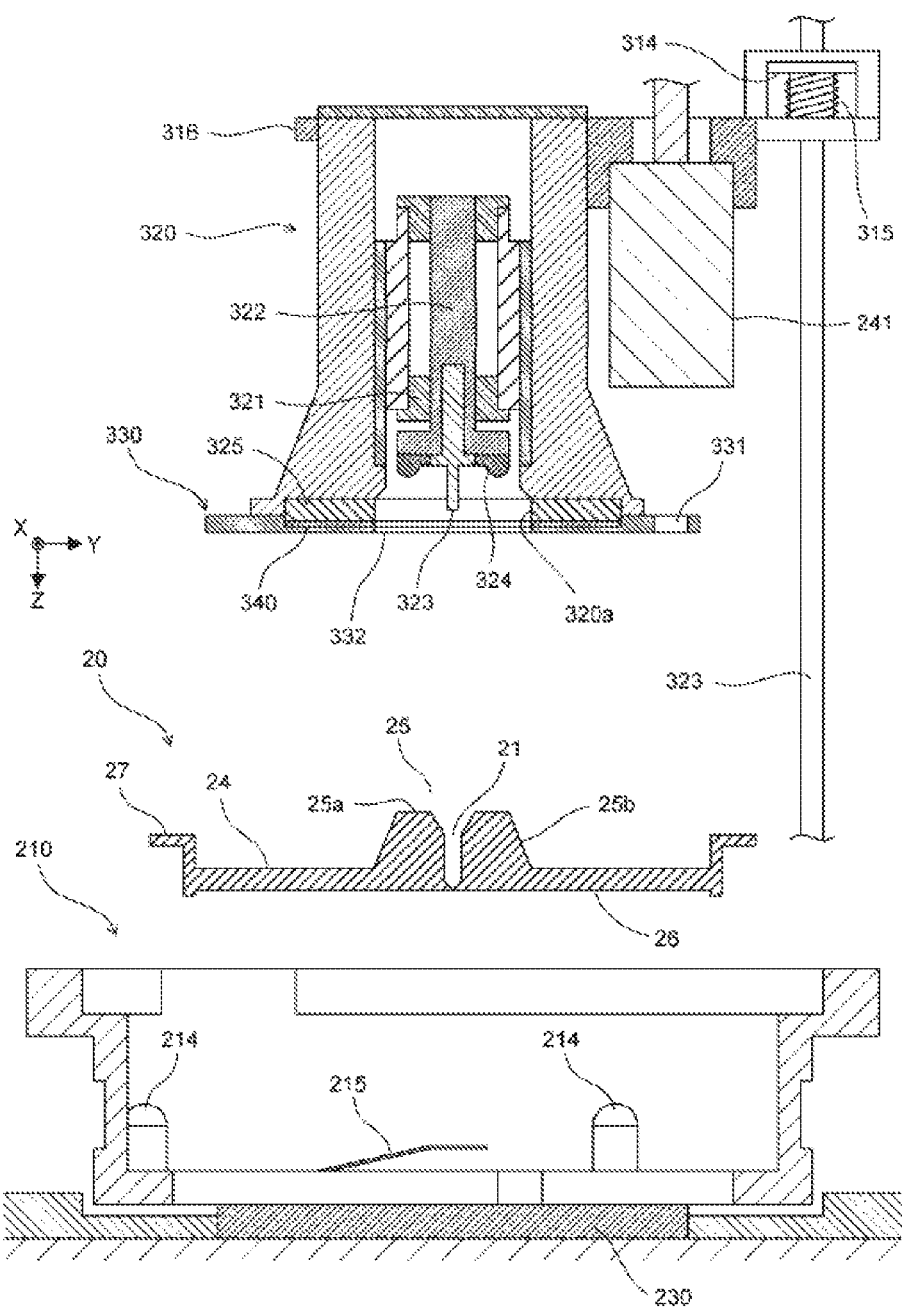
FIG. 8 is a cross-sectional view schematically illustrating a configuration of an urging part, a second container, a container setting part, and a first temperature adjustment part according to an embodiment 1.

FIG. 8 is a cross-sectional view of part of the movement mechanism 310, the supporting body 320, the holding member 330, the container setting part 210, and the second container 20 positioned right above the container setting part 210, the cross-sectional view being taken along a plane parallel to the YZ-plane through the injection port 21 of the second container 20.

As illustrated in FIG. 8, the supporting body 320 has a hole 320a penetrating in the vertical direction. The supporting body 320 includes a bearing section 321, a support member 322, a shaft member 323, a receiving member 324, and a thermal insulating member 325 in the hole 320a. The bearing section 321 is fixed to the hole 320a. The support member 322 is supported by the bearing section 321 so as to be rotatable about a central axis extending in the vertical direction.

The shaft member 323 is provided at the lower end of the support member 322 so as to be located at a position corresponding to a rotation axis of the support member 322. The shaft member 323 is formed so that the diameter of the shaft of a lower end portion is slightly smaller than the diameter of the injection port 21. Consequently, the shaft member 323 is fitted in the injection port 21 of the second container 20, and thus backflow of liquid from the injection port 21 is suppressed. Also, the shaft member 323 is a shaft regulation part that is engaged with the injection port 21 of the second container 20 set in the container setting part 210, and regulates the rotation axis of the second container 20. The receiving member 324 is provided at the lower surface of the support member 322 so as to enclose the shaft member 323. The receiving member 324 is made of fluoro-rubber. The receiving member 324 has a circular shape having a hole penetrating vertically at a central portion in a plan view, and the outer circumferential portion of the lower surface rises downward.

The urging part 300 includes a second temperature adjustment part 340. The second temperature adjustment part 340 is provided at the lower surface of the supporting body 320 via the thermal insulating member 325. The second temperature adjustment part 340 adjusts the temperature of the second container 20 set in the container setting part 210. Specifically, the second temperature adjustment part 340 is a heater, and heats the second container 20 by heating the upper surface of the upper surface section 24 of the second container 20.

The holding member 330 is provided at the lower surface of the second temperature adjustment part 340 and the lower surface of the supporting body 320, and the diameter of the outline of the holding member 330 is greater than the diameter of the outline of the supporting body 320. The holding member 330 holds an area overlapping with the twenty-three storages 22 of the second container 20, and has a hole 331 penetrating vertically at a position corresponding to the storages 22. The detector 240 performs detection on the storages 22 via the hole 331. A hole 332 penetrating vertically through the holding member 330 is formed at the center of the holding member 330 in a plan view.

The first temperature adjustment part 230 has a temperature control surface that covers an entire area from the center position of the second container 20 to at least radial positions corresponding where the storages 22 are disposed, the entire area being part of the lower surface of the lower surface section 26 of the second container 20 set in the container setting part 210. In other words, the diameter of the first temperature adjustment part 230 is set greater than or equal to the diameter of a circle where at least the storages 22 are arranged. Consequently, the temperature control of the storages 22 can be smoothly performed.

When the second container 20 is set in the container setting part 210, the lower surface of the flange section 27 is supported by the elastic members 215, and the lower surface of the lower surface section 26 of the second container 20 is separated from the upper surface of the first temperature adjustment part 230. In other words, the elastic members 215 is configured to keep the second container 20 away from the first temperature adjustment part 230. When temperature control is performed on the second container 20 in this state, the urging part 300 is configured to cause the second container 20 set in the container setting part 210 to move in the direction toward the first temperature adjustment part 230 against urging by the elastic members 215. Specifically, the holding member 330 holds the second container 20 downward by the movement of the support section 314 downward, and the lower surface of the lower surface section 26 of the second container 20 is in a state of contact with the upper surface of the first temperature adjustment part 230.

Figure 9A:
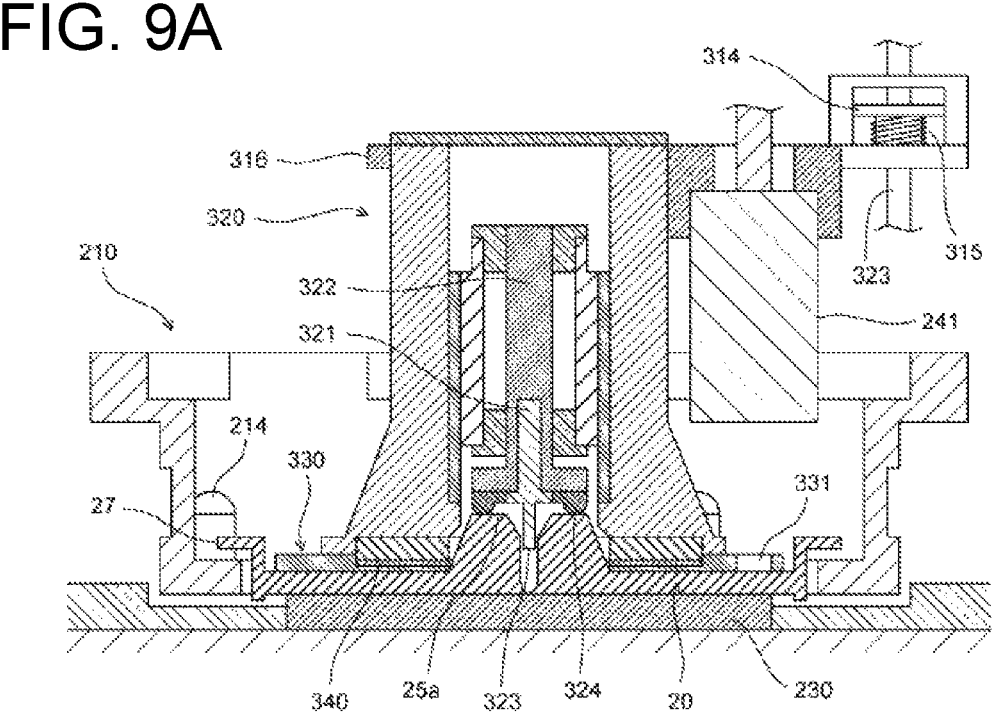
FIGS. 9A and 9B are cross-sectional views schematically illustrating a positional relationship between an urging part, a second container, a container setting part, and a first temperature adjustment part when a holding member is positioned at a first position according to an embodiment 1.

After the lower surface of the lower surface section 26 comes into contact with the upper surface of the first temperature adjustment part 230, the support section 314 is further moved downward, and thus the spring 315 is depressed as illustrated in FIG. 9A. The second container 20 is then pressed against the first temperature adjustment part 230 via the support member 316, the supporting body 320, and the holding member 330. When the holding member 330 comes into contact with and holds down the second container 20 like this, the position of the holding member 330 is referred to as the "first position" hereinafter. The first temperature adjustment part 230 and the second temperature adjustment part 340 perform temperature control on the second container 20 with the holding member 330 positioned at the first position. It is to be noted that the first position, and the later-described second position and the third position are stored in the later-described storage part 402, and are read from the storage part 402 when a control part 405 drives the urging part 300 to move the holding member 330 to specific position.

It is assumed that when temperature control is performed on the second container 20, liquid flows backward and is dispersed through the injection port 21 due to expansion of the air and liquid inside the second container 20. However, as illustrated in FIG. 9A, when the holding member 330 is positioned at the first position, the receiving member 324 is pressed against the upper surface section 25a of the projection 25, and the shaft member 323 is inserted in the injection port. Consequently, the upper portion of the injection port 21 is in a state of being sealed by the receiving member 324 and the shaft member 323, thus it is possible to prevent scattering of liquid that flows backward through the injection port 21.

Figure 10A:
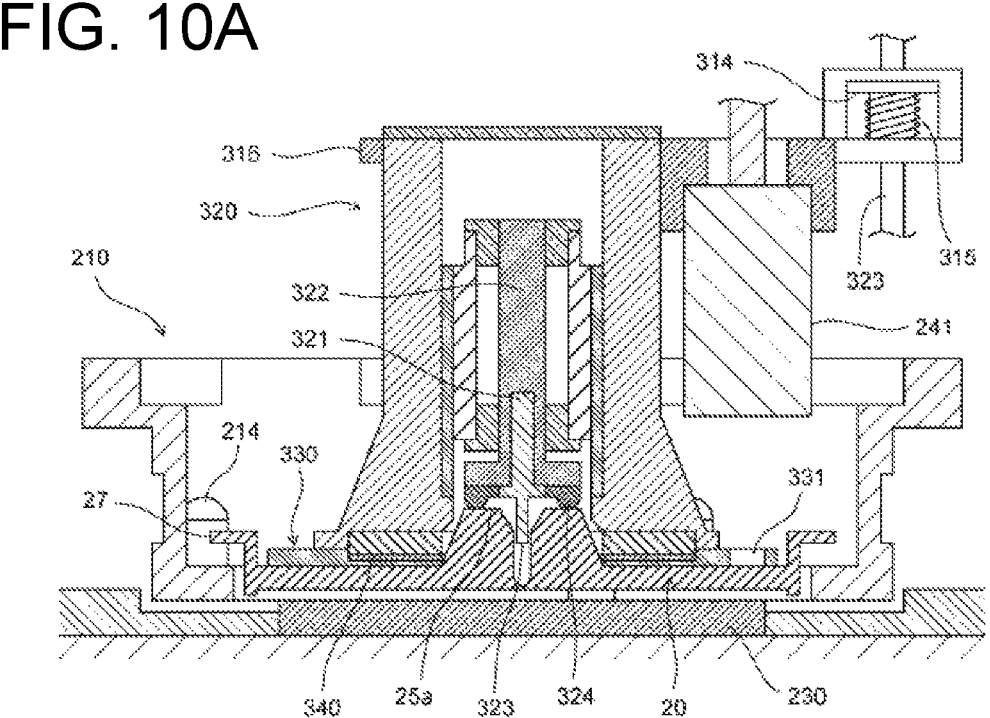
FIGS. 10A and 10B are cross-sectional views schematically illustrating a positional relationship between an urging part, a second container, a container setting part, and a first temperature adjustment part when a holding member is positioned at a second position according to an embodiment 1.
Figure 10B:
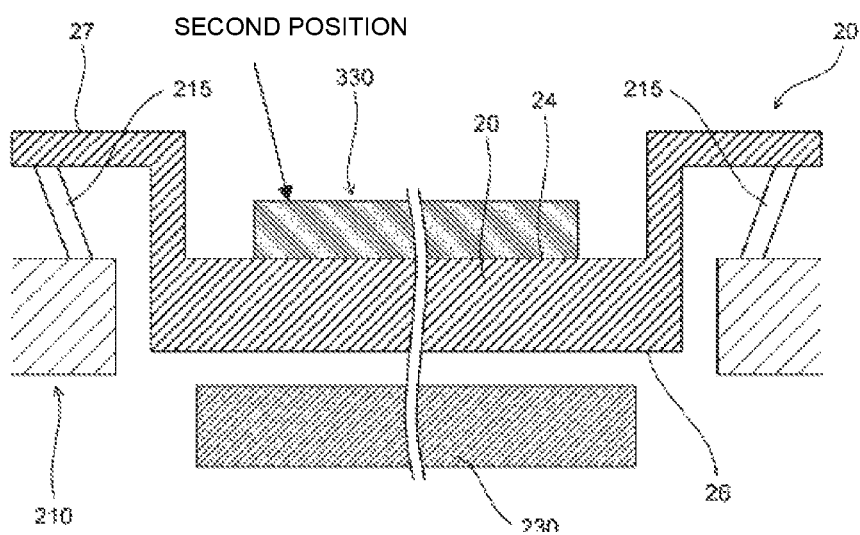

Next, when extraction liquid injected into the injection port 21 is supplied to the storages 22 by rotating the second container 20, as illustrated in FIGS. 10A and 10B, the holding member 330 is positioned so as to be in contact with the upper surface section 24 of the second container 20 slightly. At this point, the holding member 330 slightly holds down the upper surface of the upper surface section 24 of the second container 20 supported by the elastic members 215, and the elastic members 215 are in a state of being slightly depressed. Thus, in the state of FIGS. 10A and 10B, the container setting part 210 is rotated at a high speed, and even when the second container 20 is rotated at a high speed, vertical movement of the second container 20 is suppressed. When the second container 20 is rotated at a high speed, the position of the holding member 330 is referred to as the "second position" hereinafter. The second position is a position further away from the first temperature adjustment part 230 than the first position, and for regulating vertical movement of the second container 20. The rotation drive part 220 rotates the container setting part 210 at a high speed with the holding member 330 positioned at the second position, thereby rotating the second container 20 at a high speed.

When the holding member 330 is positioned at the second position, the shaft member 323 is inserted in the injection port 21, and the receiving member 324 is in a state of contact with the upper surface section 25a of the projection 25. When the second container 20 is rotated at a high speed in this state, the shaft member 323 and the receiving member 324 are rotated, and the support member 322, in which the shaft member 323 and the receiving member 324 are set, is rotated. Consequently, when the second container 20 is rotated at a high speed, the rotation axis of the second container 20 is regulated, and the second container 20 is smoothly rotated.

Figure 11A:
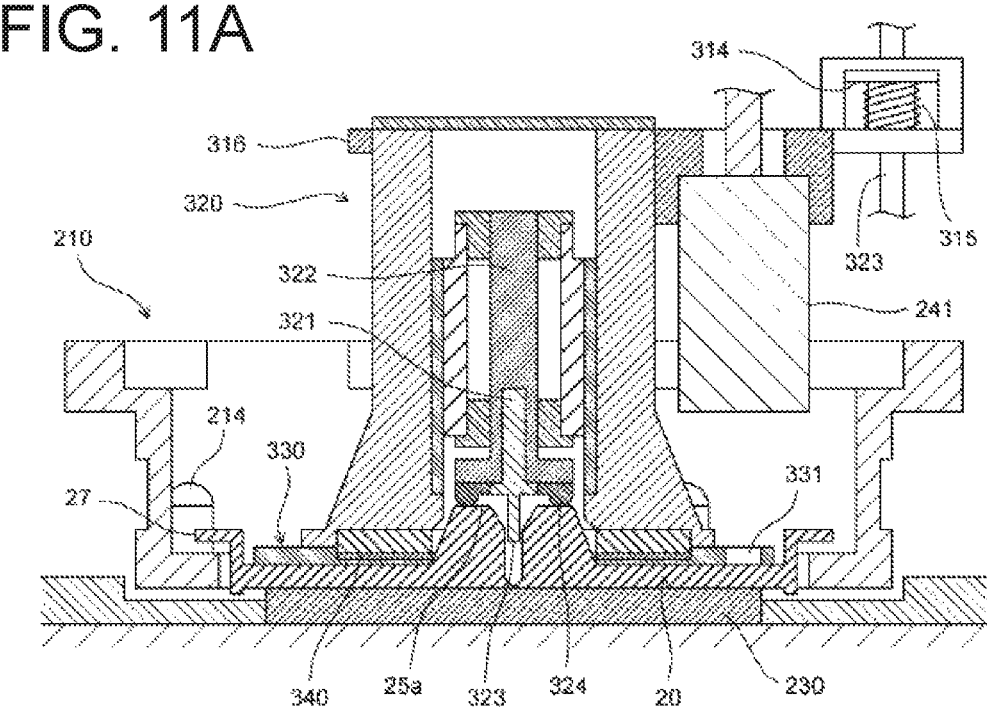
FIGS. 11A and 11B are cross-sectional views schematically illustrating a positional relationship between an urging part, a second container, a container setting part, and a first temperature adjustment part when a holding member is positioned at a third position according to an embodiment 1.
Figure 11B:
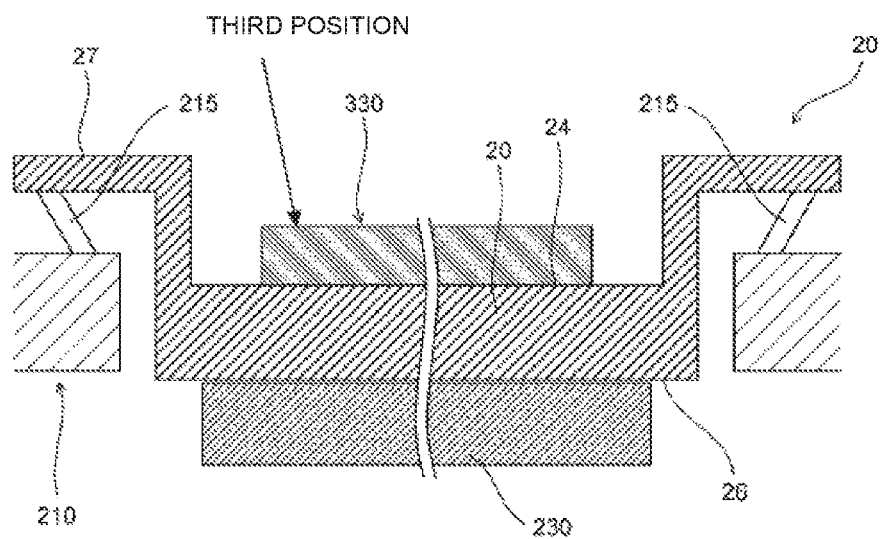

Next, when a nucleic acid amplification reaction which occurs in the storages 22 of the second container 20 is detected, as illustrated in FIGS. 11A and 11B, the lower surface section 26 of the second container 20 is not held down to, but is in a state of contact with the upper surface of the first temperature adjustment part 230 slightly. The position of the holding member 330 in this situation is referred to as the "third position" hereinafter. The third position is a position between the first position and the second position, and more specifically, a position slightly displaced upward from the first position. The detector 240 detects a nucleic acid amplification reaction in the storages 22 of the second container 20 with the holding member 330 positioned at the third position.

When the holding member 330 is positioned at the third position, the second container 20 is pressed upward by the elastic members 215, and is held down by the holding member 330. Consequently, the vertical position of the second container 20 is located at a predetermined position, thus the focal position of excitation light, with which an irradiation position is irradiated from the detection head 241 through the hole 331, can be positioned at a desired vertical position in the storages 22.

Figure 12:
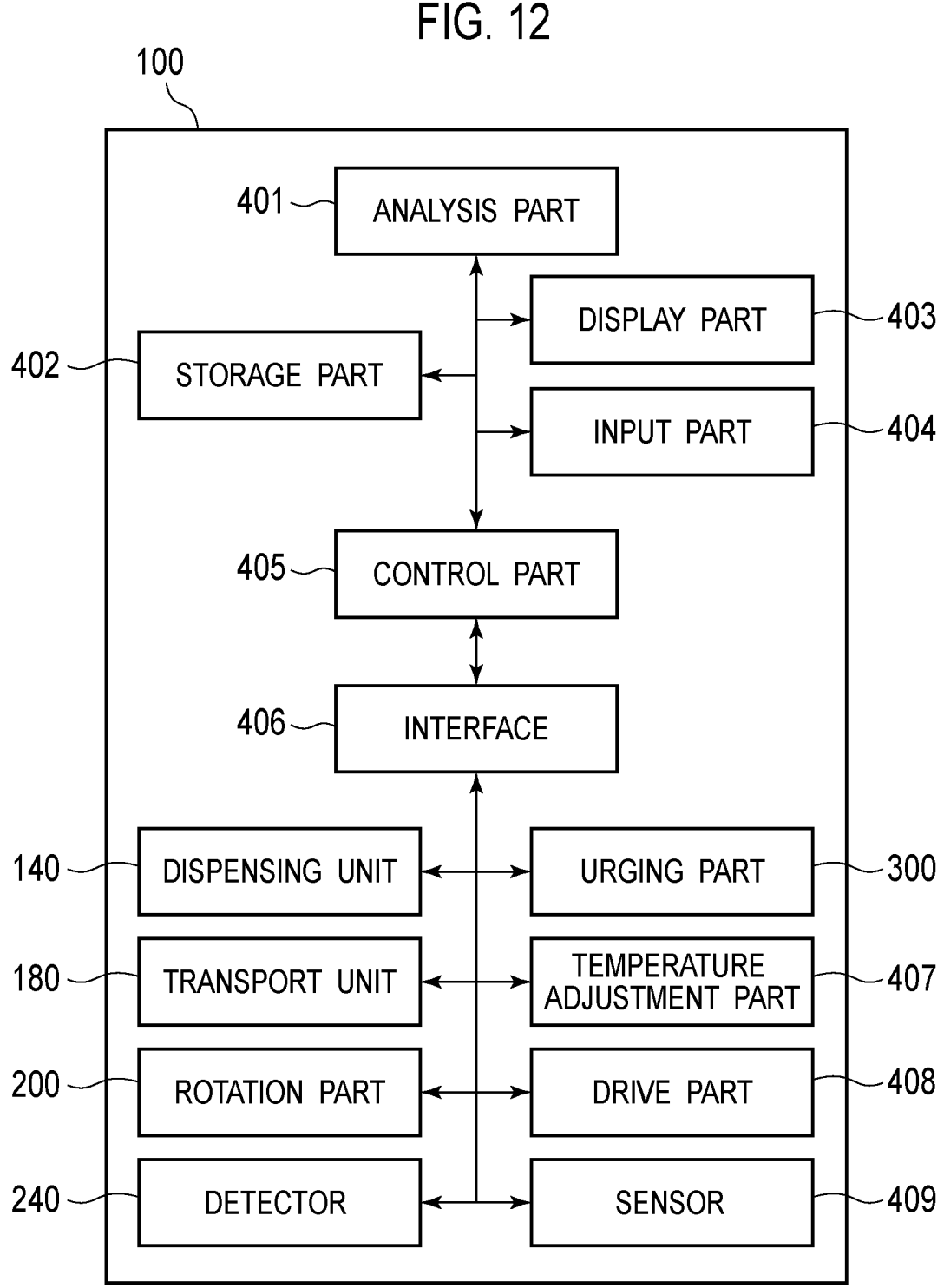
FIG. 12 is a block diagram illustrating a configuration of a nucleic acid analyzer according to an embodiment 1.

As illustrated in FIG. 12, the nucleic acid analyzer 100 includes the dispensing unit 140, the transport unit 180, the rotation part 200, the detector 240, and the urging part 300 as described above. In addition, the nucleic acid analyzer 100 includes an analysis part 401, a storage part 402, a display part 403, an input part 404, a control part 405, an interface 406, a temperature adjustment part 407, a drive part 408, and a sensor 409.

The analysis part 401 includes a CPU (Central Processing Unit). When receiving a start instruction via the input part 404, the analysis part 401 transmits an instruction signal to the control part 405 to start nucleic acid analysis processing. The analysis part 401 generates pieces of time series data from an electrical signal of fluorescence detected by the detector 240, the pieces of time series data indicating a nucleic acid amplification reaction which occurs in each storage 22 of the second container 20. The analysis part 401 determines positive or negative for detection target nucleic acid in which a detection target region of nucleic acids has mutated, based on the generated time series data.

The storage part 402 includes a RAM, a ROM, a hard disk, or the like. The display part 403 includes a display. The input part 404 includes a keyboard, a mouse, and the like. Instead of the display part 403 and the input part 404, the nucleic acid analyzer 100 may include a display input part including a touch-screen display.

The control part 405 includes a CPU or a microcomputer. The control part 405 controls the dispensing unit 140, the transport unit 180, the rotation part 200, the detector 240, the urging part 300, the temperature adjustment part 407, the drive part 408, and the sensor 409 via the interface 406. The temperature adjustment part 407 includes the temperature adjustment parts 150, 160, the first temperature adjustment part 230, and the second temperature adjustment part 340. The drive part 408 includes various drive parts disposed in the nucleic acid analyzer 100. The sensor 409 includes various sensors disposed in the nucleic acid analyzer 100.

Next, the processing of nucleic acid analyzer 100 is described.

When a sample is analyzed by the nucleic acid analyzer 100, an operator sets a new first container 10 in the first container setting part 110, and stores the sample in the reaction part 11 of the first container 10. A sample in an embodiment 1 is a formalin-fixed paraffin-embedded (FFPE) tissue section. The operator stores ethanol in the reagent storage 15. In addition, the operator sets a new second container 20 in the second container setting part 120. The new second container 20 stores reagents for amplification and fluorescent labeling of different detection target nucleic acids in the storages 22. In addition, the operator sets a new third container 30 in the third container setting part 130.

It is to be noted that the nucleic acid analyzer 100 can perform nucleic acid analysis concurrently for three samples. As described above, the nucleic acid analyzer 100 includes three sets each containing the first container setting part 110, the second container setting part 120, and the third container setting part 130 which are arranged along the X-axis direction, and one set is used for one sample. When nucleic acid analysis is concurrently performed on multiple samples, an operator sets the first container 10, the second container 20, and the third container 30 for each of multiple sets. Hereinafter, the steps of nucleic acid analysis in one set are described.

Figure 13:
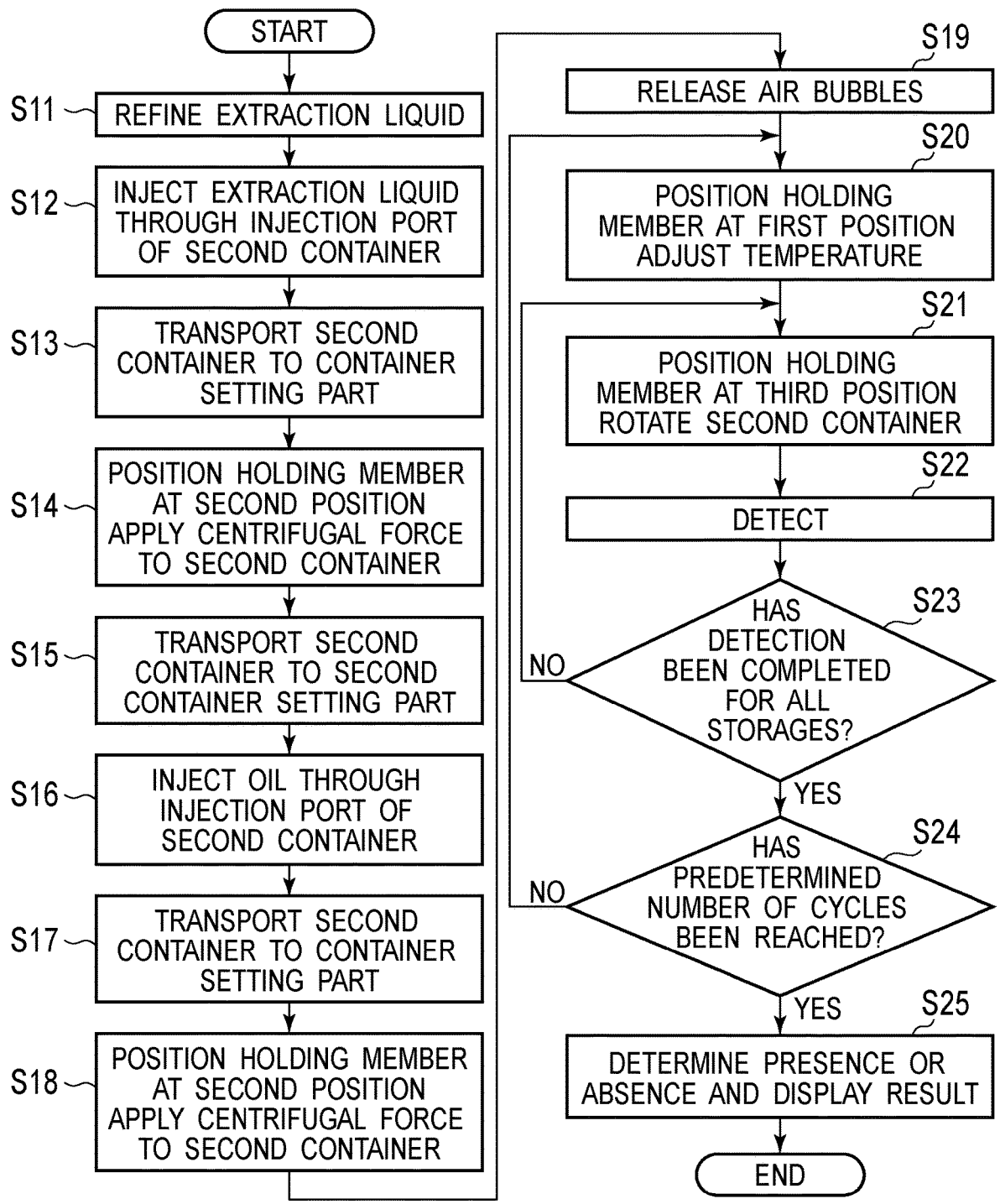
FIG. 13 is a flowchart illustrating processing of a nucleic acid analyzer according to an embodiment 1.

As illustrated in FIG. 13, when analysis of nucleic acid is started, the control part 405 drives the dispensing unit 140, and mounts the piercing tip 31 on the lower end of the aspiration part 141. The control part 405 drives the dispensing unit 140 to pierce the aluminum seal 10*a* with the piercing tip 31, thereby opening the top of the reagent storage 12, the reagent storages 13*a* to 13*h*, and the waste fluid storage 16 of the first container 10. In step S11, the control part 405 drives the dispensing unit 140 to refine the extraction liquid in the first container 10. In the following dispensation, the pipette tip 32 is mounted on or replaced from the aspiration part 141 as appropriate, and liquid is aspirated or discharged by the aspiration part 141 through the pipette tip 32.

In step S11, specifically, the control part 405 performs the following control. The control part 405 dispenses solubilized solution of the reagent storage 13*a* to the reaction part 11. Thus, a FFPE (Formalin Fixation and Paraffin Embedding) section is immersed. The control part 405 moves the temperature adjustment part 150 upward, and heats the reaction part 11 with the heater 152. Thus, paraffin is melted.

Next, the control part 405 dispenses proteinase K of the reagent storage 13*b* to the reaction part 11, and dispenses oil of the reagent storage 13*c* to the reaction part 11. The oil of the reagent storage 13*c* is mineral oil. Subsequently, the control part 405 adjusts the temperature of the reaction part 11 by the temperature adjustment part 150. Thereby, the protein in the reaction part 11 is broken down and nucleic acids are extracted from cells.

Next, the control part 405 brings the magnetic force application part 170 close to the reagent storage 12. Accordingly, magnetic particles in the reagent storage 12 are collected at the wall surface of the reagent storage 12. The control part 405 then drives the dispensing unit 140 to transport magnetic particle preservation solution in the reagent storage 12 to the waste fluid storage 16. The control part 405 then keeps the magnetic force application part 170 away from the reagent storage 12. Subsequently, the control part 405 drives the dispensing unit 140 to dispense ethanol of the reagent storage 15, and reagents for extraction of the reagent storage 13*e* to the mixing part 14*c*, and dispenses a mixed solution of the ethanol and the reagents for extraction stored in the mixing part 14*c* to the reagent storage 12.

Subsequently, the control part 405 drives the dispensing unit 140 to move the sample solution in the reaction part 11 to the reagent storage 12, and agitates the sample solution in the reagent storage 12 by repeating aspiration and discharge in the reagent storage 12. Subsequently, the control part 405 drives the temperature adjustment part 160 to adjust the temperature of the reagent storage 12. Thus, nucleic acids are captured by the magnetic particles. Subsequently, the control part 405 brings the magnetic force application part 170 close to the reagent storage 12. Thus, the magnetic particles in the reagent storage 12 are collected at the wall surface of the reagent storage 12. The control part 405 then drives the dispensing unit 140 to aspirate supernatant of the reagent storage 12, and transports the aspirated liquid to the waste fluid storage 16. The control part 405 then keeps the magnetic force application part 170 away from the reagent storage 12.

Next, the control part 405 drives the dispensing unit 140 to dispense ethanol of the reagent storage 15, and undiluted first cleaning solution of the reagent storage 13*h* to the mixing part 14*b*, and dispenses a mixed solution of the ethanol and the undiluted first cleaning solution stored in the mixing part 14*b* to the reagent storage 12. Subsequently, the control part 405 drives the dispensing unit 140 to agitate the sample solution in the reagent storage 12. Subsequently, the control part 405 brings the magnetic force application part 170 close to the reagent storage 12. The control part 405 then controls the dispensing unit 140 to aspirate supernatant of the reagent storage 12, and transports the aspirated liquid to the waste fluid storage 16. The control part 405 then keeps the magnetic force application part 170 away from the reagent storage 12.

Similarly, the control part 405 drives the dispensing unit 140 to dispense ethanol of the reagent storage 15, and undiluted second cleaning solution of the reagent storage 13*f* to the mixing part 14*d*, and dispenses a mixed solution of the ethanol and the undiluted second cleaning solution stored in the mixing part 14*d* to the reagent storage 12. Subsequently, the control part 405 drives the dispensing unit 140 to agitate the sample solution in the reagent storage 12. Subsequently, the control part 405 brings the magnetic force application part 170 close to the reagent storage 12. The control part 405 then drives the dispensing unit 140 to aspirate supernatant of the reagent storage 12, and transports the aspirated liquid to the waste fluid storage 16. The control part 405 then keeps the magnetic force application part 170 away from the reagent storage 12. In this manner, impurities in the reagent storage 12 are washed and removed.

Although impurities are washed and removed in an embodiment 1, washing of impurities may be omitted. In other words, extraction liquid without removing impurities may be injected into the injection port 21 of the second container 20.

Subsequently, the control part 405 drives the dispensing unit 140 to dispense the eluate of the reagent storage 13*d* to the reagent storage 12, and agitates the sample solution in the reagent storage 12. Subsequently, the control part 405 drives the temperature adjustment part 160 to adjust the temperature of the reagent storage 12. Thus, the nucleic acids in the reagent storage 12 are eluted from the magnetic particles.

Next, the control part 405 brings the magnetic force application part 170 close to the reagent storage 12. Thus, the magnetic particles in the reagent storage 12 are collected at the wall surface of the reagent storage 12. Subsequently, the control part 405 drives the dispensing unit 140 to transport the sample solution of the reagent storage 12 to the mixing part 14a. The control part 405 then keeps the magnetic force application part 170 away from the reagent storage 12. Subsequently, the control part 405 dispenses undiluted solution of diluent of the reagent storage 13g to the mixing part 14a, and agitates the sample solution in the mixing part 14a. Thus, the concentration of the sample of the mixing part 14a is adjusted, and the extraction liquid is completed.

In step S12, the control part 405 drives the dispensing unit 140 to inject the extraction liquid of the mixing part 14a into the injection port 21 of the second container 20 set in the second container setting part 120. In step S13, the control part 405 drives the transport unit 180 to transport the second container 20 set in the second container setting part 120 to the container setting part 210, and sets the second container 20 in the container setting part 210. In step S14, the control part 405 drives the urging part 300 to position the holding member 330 at the second position as illustrated in FIGS. 10A and 10B, drives the rotation part 200 to rotate the second container 20 at a high speed, and applies a centrifugal force to the second container 20. At this point, the rotation part 200 rotates the second container 20 at 4500 rpm for 5 seconds. It is to be noted that to supply the extraction liquid injected into the injection port 21 to each storage 22 through a corresponding flow path 23, it is desirable that the rotational speed of the second container 20 be 1000 rpm or higher.

In step S15, the control part 405 drives the transport unit 180 to transport the second container 20 rotated by the rotation part 200 to the second container setting part 120. In step S16, the control part 405 drives the dispensing unit 140 to inject the oil of the reagent storage 13c into the injection port 21 of the second container 20 which has been rotated by the rotation part 200 and transported to the second container setting part 120.

Subsequently, in step S17, the control part 405 drives the transport unit 180 to transport the second container 20 with the oil injected to the position of the rotation part 200 again, and sets the second container 20 in the container setting part 210. In step S18, the control part 405 drives the urging part 300 to position the holding member 330 at the second position as illustrated in FIGS. 10A and 10B, drives the rotation part 200 to rotate the second container 20 at a high speed, and applies a centrifugal force to the second container 20. At this point, the rotation part 200 rotates the second container 20 at 4500 rpm for 3 seconds. Consequently, the air in the flow path 23 of the second container 20 is replaced by the oil which is injected through the injection port 21.

Next, in steps S19 to S25, detection of a nucleic acid amplification reaction and nucleic acid analysis are performed. In an embodiment 1, detection and analysis are performed based on the principle of BNA (Bridged Nucleic Acids) clamp PCR. It is to be noted that the principle of detection and analysis is not limited to the BNA clamp PCR, and may be PCR+Invader, for instance.

Figure 9B:
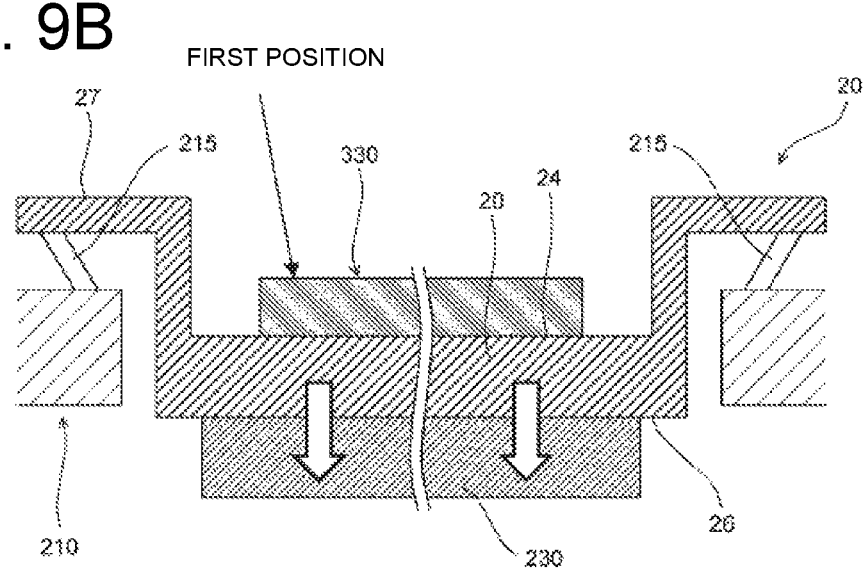

In step S19, the control part 405 releases air bubbles inside the second container 20 through the injection port 21. Specifically, the control part 405 drives the urging part 300 to position the holding member 330 at the first position as illustrated in FIGS. 9A and 9B. The control part 405 increases the temperature of the first temperature adjustment part 230 and the second temperature adjustment part 340 up to 94° C., then turns off the second temperature adjustment part 340 to decrease the temperature of the first temperature adjustment part 230 down to 57° C. Thus, after the temperature of the second container 20 is increased close to 94° C., the temperature of the second container 20 is decreased close to 57° C.

Subsequently, the control part 405 drives the urging part 300 to position the holding member 330 at the second position as illustrated in FIGS. 10A and 10B, and drives the rotation part 200 to rotate the second container 20 at a high speed. At this point, the rotation part 200 rotates the second container 20 at 4500 rpm for 5 seconds. Thus, a centrifugal force is applied to the second container 20, and air bubbles in the second container 20 are released through the injection port 21.

Figure 14A:
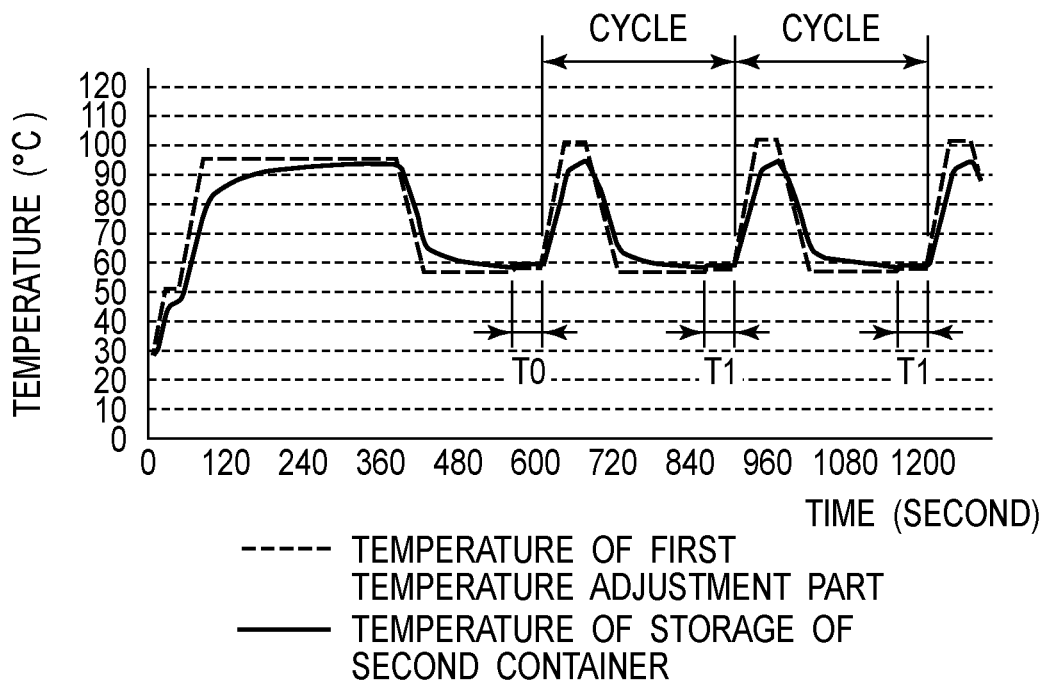
FIG. 14A is a chart illustrating an example of a graph depicting a relationship between elapsed time and temperature according to an embodiment 1.

In the example illustrated in FIG. 14A, after the temperature of the first temperature adjustment part 230 and the second temperature adjustment part 340 is increased up to approximately 96° C., the second temperature adjustment part 340 is turned off, and the temperature of the first temperature adjustment part 230 is decreased down to approximately 57° C. Thus, after the temperature of the second container 20 is increased close to 94° C., the temperature of the second container 20 is decreased close to 58° C. Subsequently, in an interval T0, the temperature of the first temperature adjustment part 230 is slightly increased, and the second container 20 is rotated by the rotation part 200 to release air bubbles.

Returning to FIG. 13, in step S20, the control part 405 drives the urging part 300 to position the holding member 330 at the first position as illustrated in FIGS. 9A and 9B. The control part 405 increases the temperature of the first temperature adjustment part 230 and the second temperature adjustment part 340 up to a first temperature, turns off the second temperature adjustment part 340, and decreases the temperature of the first temperature adjustment part 230 down to a second temperature lower than the first temperature, thereby performing temperature control on the second container 20. In an embodiment 1, the first temperature is, for instance, 94° C. and the second temperature is, for instance, 57° C. Thus, after the temperature of the second container 20 is increased close to 94° C., the temperature of the second container 20 is decreased close to 57° C.

Subsequently, in step S21, the control part 405 drives the urging part 300 to position the holding member 330 at the third position as illustrated in FIGS. 11A and 11B, drives the rotation part 200 to rotate the second container 20 so that the storages 22 are positioned at the detection position of the detector 240. In step S22, the control part 405 drives the detector 240 with the holding member 330 maintained at the third position, and detects a nucleic acid amplification reaction which occurs in the storages 22. Specifically, the detector 240 irradiates the storages 22 with excitation light through the hole 331 of the holding member 330, and receives fluorescence which has occurred from the storages 22 by the light detector 242d. The control part 405 acquires the fluorescence intensity based on an electrical signal outputted by the light detector 242d and stores the acquired fluorescence intensity in the storage part 402.

In step S23, the control part 405 determines whether or not detection for all the storages 22 is completed. When detection for all the storages 22 is not completed, the control part 405 returns the processing to step S21. In this case, in step S21, the control part 405 drives the rotation part 200 with the holding member 330 positioned at the third position to rotate the second container 20 only by a pitch in the circumferential direction in which the storages 22 are arranged so that the adjacent storage 22, in which detection is not completed yet, is positioned at the detection position.

As described above, in step S22, a nucleic acid amplification reaction is detected through the hole 331 of the holding member 330.

In this manner, the operation of the rotation drive part 220 to rotate the second container 20 only by a pitch in the circumferential direction in which the storages 22 are arranged in a state where the holding member 330 is positioned at the third position by the urging part 300, and the operation of the detector 240 to detect a nucleic acid amplification reaction in the storage 22 in a state where the holding member 330 is maintained at the third position by the urging part 300 are repeated. Then, a nucleic acid amplification reaction is detected sequentially from all the storages 22 disposed side by side in the circumferential direction. In this manner, when the state where the holding member 330 is positioned at the third position is maintained, a state where the lower surface of the lower surface section 26 of the second container 20 is in contact with the upper surface of the first temperature adjustment part 230 is maintained. Consequently, the temperature of the second container 20 can be appropriately maintained.

It is to be noted that in an embodiment 1, the adjacent storage 22 is sequentially positioned at the detection position while the second container 20 is being rotated in a certain direction, however, a non-adjacent storage 22 may be sequentially positioned at the detection position. For instance, when detection of a first storage 22 is completed, a second storage 22 located forward by two positions in the clockwise direction from the first storage 22 may be positioned at the detection position, and when detection of the second storage 22 is completed, a third storage 22 located backward by one position in the counterclockwise direction from the second storage 22 may be positioned at the detection position.

When detection of all the storages 22 is completed, in step S24, the control part 405 determines whether or not the number of cycles has reached a predetermined number of cycles. Here, each cycle is the processing in steps S20 to S23. The predetermined number of cycles is, for instance, 55 cycles. In other words, in step S24, it is determined whether or not a cycle including the steps S20 to S23 has been repeated for a predetermined number of cycles in total. When the number of cycles has not reached the predetermined number of cycles, the control part 405 returns the processing to step S20. The control part 405 again performs the cycle including the steps S20 to S23.

In the example illustrated in FIG. 14A, in one cycle, after the temperature of the first temperature adjustment part 230 and the second temperature adjustment part 340 is increased up to approximately 102° C., the second temperature adjustment part 340 is turned off, and the temperature of the first temperature adjustment part 230 is decreased down to approximately 57° C. Thus, after the temperature of the second container 20 is increased close to 95° C., the temperature of the second container 20 is decreased close to 58° C. Subsequently, in an interval T1, the temperature of the first temperature adjustment part 230 is slightly increased, and a nucleic acid amplification reaction is detected sequentially from all the storages 22. It is to be noted that for detection of a nucleic acid amplification reaction, when the temperature of the first temperature adjustment part 230 is slightly increased as in the example of FIG. 14A, the temperature of the second container 20 is easily set to be constant, as compared with the case where the temperature of the first temperature adjustment part 230 is maintained at a constant near 58° C.

Returning to FIG. 13, when the number of cycles reaches a predetermined number of cycles, in step S25, the analysis part 401 determines the presence or absence of detection target nucleic acid in each storage 22, and displays a result of the determination, and the like, on the display part 403. Thus, the processing of nucleic acid analysis for one sample is completed. When the processing of nucleic acid analysis for one sample is completed, the control part 405 drives the transport unit 180 to transport the second container 20 set in the container setting part 210 to the second container setting part 120. The transported second container 20 is discarded after an appropriate time.

Next, the determination processing in step S25 is described in detail.

Figure 14B:
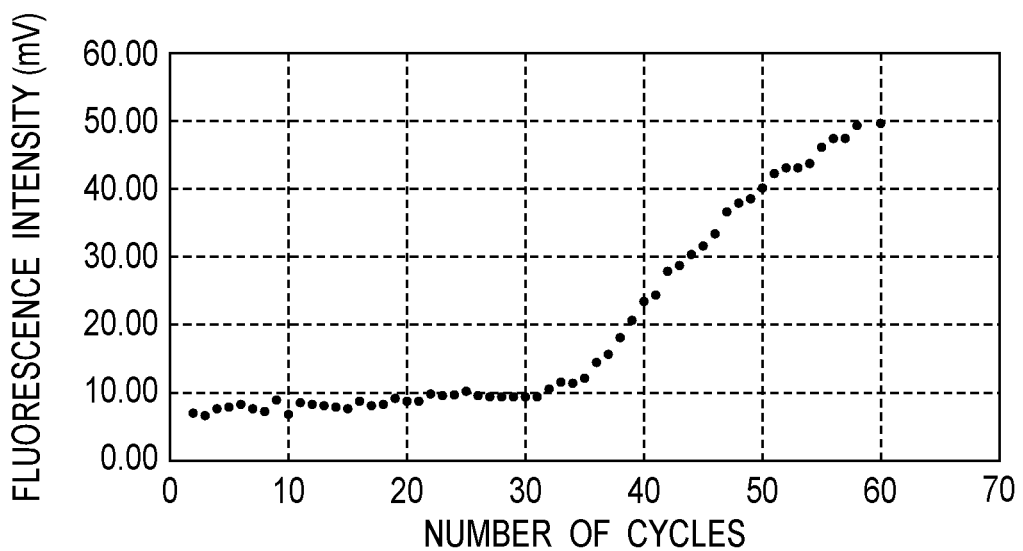
FIG. 14B is a chart illustrating an example of a graph depicting a relationship between the number of cycles and fluorescence intensity according to an embodiment 1.

As illustrated in FIG. 14B, the analysis part 401 generates a graph based on time series data which indicate the fluorescence intensities of all cycles acquired from one storage 22. FIG. 14B illustrates an example in which the total number of cycles is 59. When detection target nucleic acid is contained in a storage 22, repeated cycle processing as mentioned above causes the detection target nucleic acid to be gradually amplified by the reagents pre-stored in the storage 22. Thus, the excited fluorescence intensity is increased as the number of cycles proceeds. On the other hand, when detection target nucleic acid is not contained in a storage 22, repeated cycle processing as mentioned above does not cause any detection target nucleic acid to be amplified. Thus, the fluorescence intensity is maintained at a low value regardless of the number of cycles repeated.

Figure 15A:
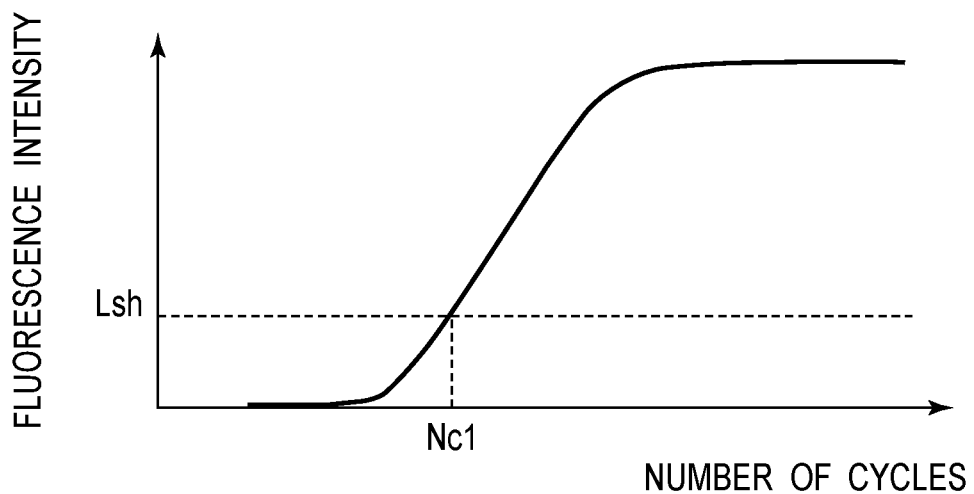
FIG. 15A is a graph for explaining acquisition of number of cycles based on a threshold for fluorescence intensity in the graph depicting a relationship between the number of cycles and fluorescence intensity according to an embodiment 1.

Subsequently, as illustrated in FIG. 15A, in the graph of the number of cycles and the fluorescence intensity, the analysis part 401 sets threshold Lsh for fluorescence intensity stored in the storage part 402. The analysis part 401 acquires the number of cycles, Nc1 when the fluorescence intensity reaches the threshold Lsh. In other words, the analysis part 401 acquires rise timing of fluorescence intensity in the graph of the number of cycles and the fluorescence intensity.

Figure 15B:
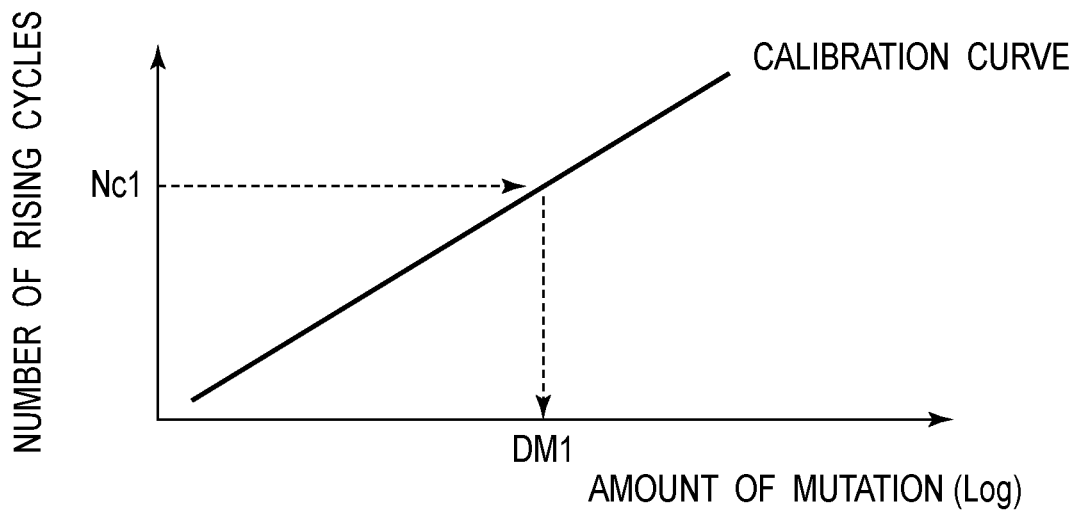
FIG. 15B is a graph for explaining acquisition of an amount of mutation based on the acquired number of cycles according to an embodiment 1.

As illustrated in FIG. 15B, in the graph of the number of rising cycles and the amount of mutation, obtained in advance using a calibration curve and stored in the storage part 402, the analysis part 401 acquires the amount of mutation, DM1 corresponding to the number of cycles, Nc1. When the acquired DM1 is greater than or equal to a cutoff value stored in the storage part 402, the analysis part 401 determines that detection target nucleic acid is present in the storage 22. On the other hand, when the acquired DM1 is less than the cutoff value stored in the storage part 402, the analysis part 401 determines that no detection target nucleic acid is present in the storage 22.

When detection target nucleic acid is determined to be present in the storage 22, the analysis part 401 makes positive determination of detection target nucleic acid for the sample, and when no detection target nucleic acid is determined to be present in the storage 22, the analysis part 401 makes negative determination of detection target nucleic acid for the sample.

Next, the display processing in step S25 is described in detail.

Figures 16A, 16B:
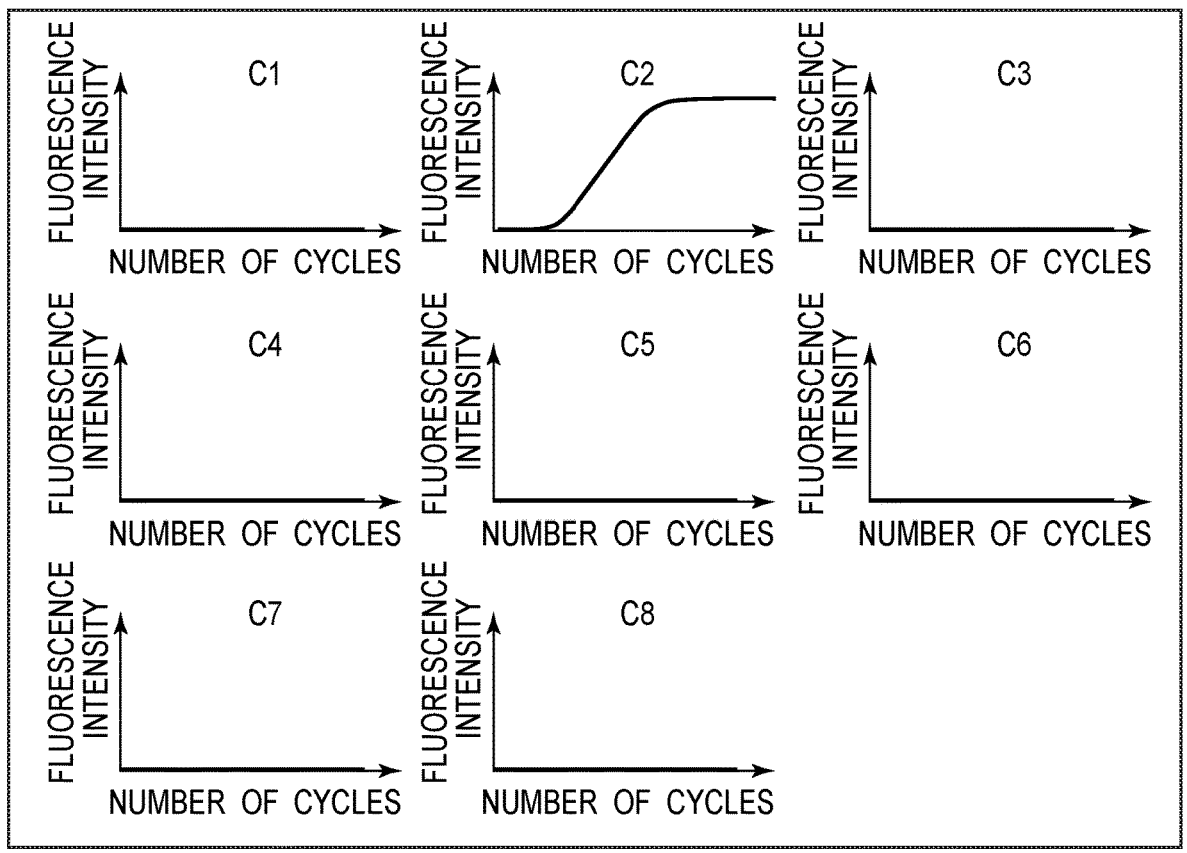
FIG. 16A is a table illustrating examples of a gene to be analyzed by a nucleic acid analyzer, the name of each storage, and the detection target nucleic acid detected in each storage according to an embodiment 1.
FIG. 16B provide charts each illustrating an example of a graph depicting a relationship between the number of cycles and fluorescence intensity based on each storage according to an embodiment 1.

The nucleic acid analyzer 100 in an embodiment 1 particularly performs analysis of DNA (deoxyribonucleic acid). In an embodiment 1, presence or absence of mutation of KRAS is determined, the KRAS being a type of cancer-related genes. For instance, as illustrated in FIG. 16A, multiple detection target nucleic acids of KRAS related to colorectal cancer are respectively detected in eight storages 22 indicated by C1 to C8. In this case, each of the eight storages 22 indicated by C1 to C8 pre-store reagents for amplifying corresponding detection target nucleic acids, and reagents containing fluorescent probes for labeling corresponding detection target nucleic acids.

When detection of a nucleic acid amplification reaction is performed as described above in each storage 22, as illustrated in FIG. 16B, the analysis part 401 generates a graph of the number of cycles and the fluorescence intensity for each storage 22. In the example illustrated in FIG. 16B, in the storage 22 indicated by C2, the fluorescence intensity increases as the number of cycles increases, and in the storages 22 indicated by C1, C3 to C8, the fluorescence intensity is not increased. In this case, the analysis part 401 makes positive determination for the detection target nucleic acid corresponding to the storage 22 indicated by C2, and makes negative determination for the detection target nucleic acid corresponding to the storages 22 indicated by C1, C3 to C8.

Figure 17:
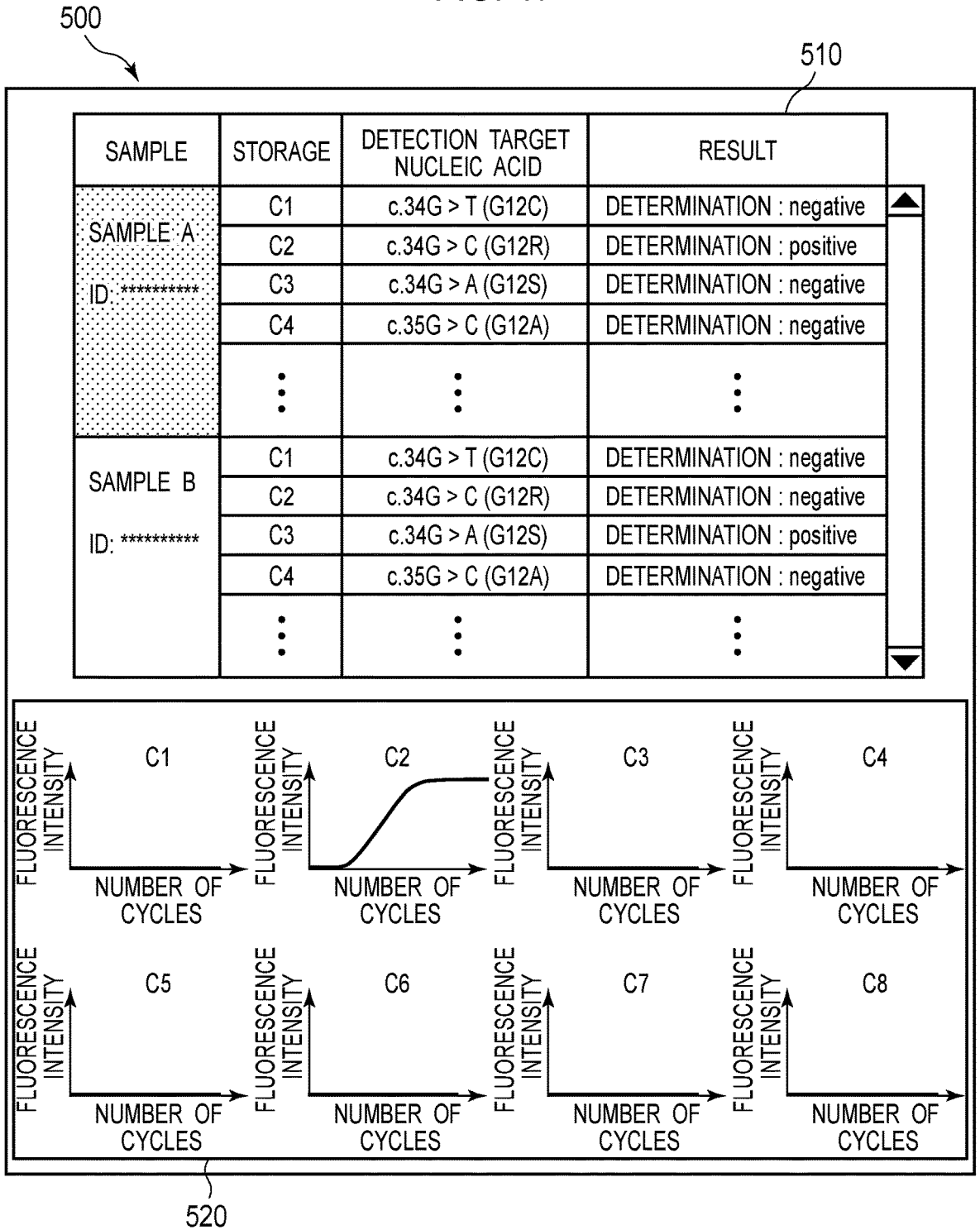
FIG. 17 is a chart schematically illustrating a result screen displayed on a display part according to an embodiment 1.

As illustrated in FIG. 17, the analysis part 401 displays a screen 500 including a list 510 and a graph area 520 on the display part 403. The list 510 displays a result of the determination of detection target nucleic acid corresponding to each storage 22 for each sample as a list. In the graph area 520, graphs based on the storages 22 are displayed for a sample selected in the list 510.

As described above, when the processing by the nucleic acid analyzer 100 is started, processing to extract nucleic acids from a sample, detection of a nucleic acid amplification reaction which occurs in each storage 22, and determination indicating presence or absence of detection target nucleic acid are automatically performed. Thus, nucleic acid analysis can be conducted by performing a minimum number of steps, such as setting samples and containers.

The nucleic acid analyzer 100 in an embodiment 1 can determine presence or absence of mutation of BRAF, PIK3CA, NRAS, EGFR, ALK Fusions, ALK Mut., and the like other than KRAS according to reagents pre-stored in the second container 20. The presence or absence of mutation of KRAS, BRAF, PIK3CA, and NRAS is useful for diagnosis of colorectal cancer, for instance. The presence or absence of mutation of KRAS, BRAF, PIK3CA, NRAS, EGFR, ALK Fusions, and ALK Mut. is useful for diagnosis of non-small cell lung cancer, for instance.

Embodiment 2

In an embodiment 2, the injection port 21 of the second container 20 set in the second container setting part 120 is positioned at a location displaced from the center of the width of the first container 10 in the Y-axis direction, in the Y-axis direction. In this case, as illustrated in FIGS. 18A and 18B, the first container setting part 110 and the second container setting part 120 are disposed so that the range of the width of the first container 10 set in the first container setting part 110 in the Y-axis direction overlaps with the range of the width of the second container 20 set in the second container setting part 120 in the Y-axis direction.

Figure 18A:
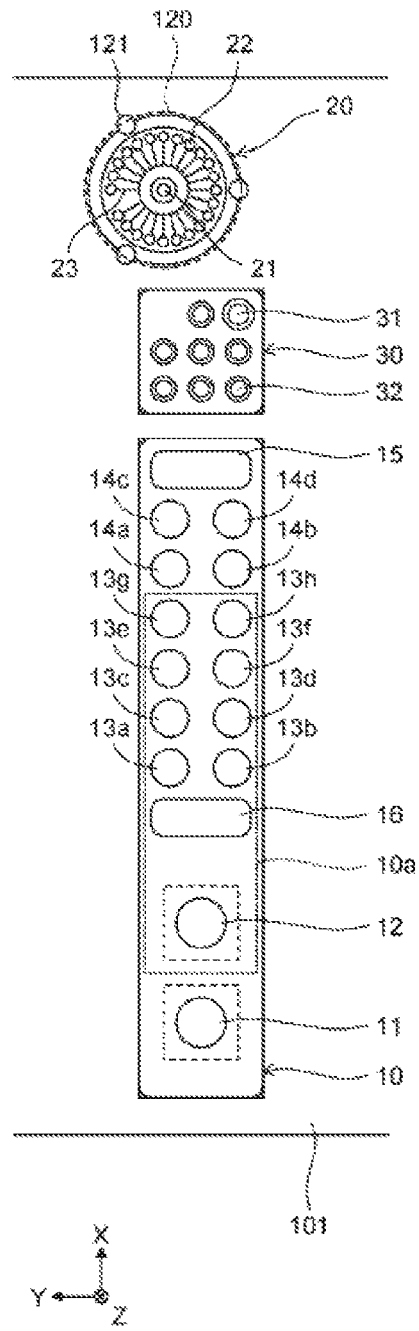
FIGS. 18A and 18B are views schematically illustrating an arrangement of a second container setting part according to an embodiment 2.

In the example illustrated in FIG. 18A, although the injection port 21 of the second container 20 is displaced in the Y-axis direction from the center of the width of the first container 10 in the Y-axis direction, the injection port 21 is positioned within the range of the width of the first container 10 in the Y-axis direction. In the example illustrated in FIG. 18B, although the injection port 21 of the second container 20 is positioned in the Y-axis direction outside the range of the width of the first container 10 in the Y-axis direction, the range of the second container 20 in the Y-axis direction overlaps with the range of the first container 10 in the Y-axis direction.

Figure 18B:
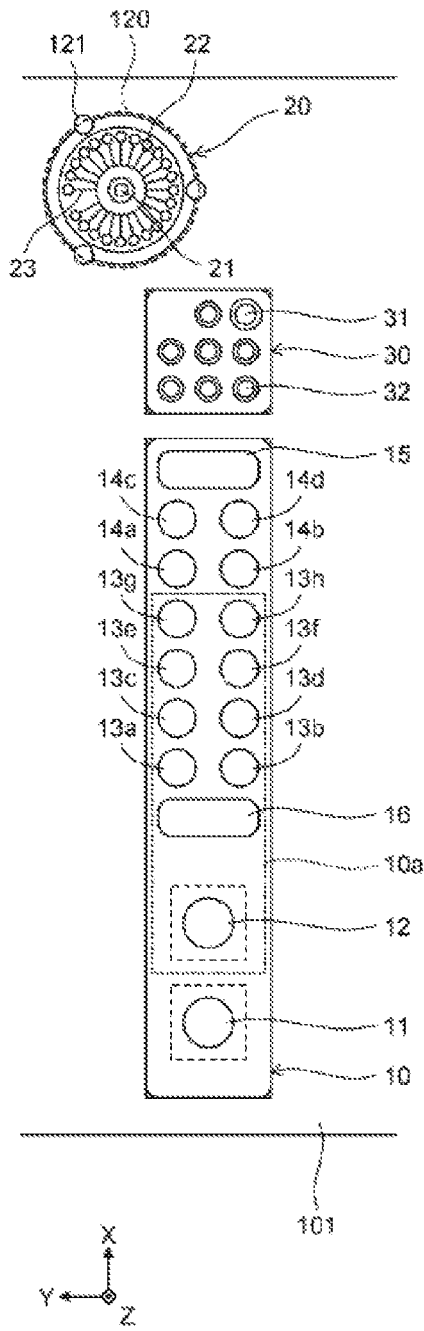

Also when the second container setting part 120 is disposed as illustrated in FIGS. 18A and 18B, the second container setting part 120 is disposed on the positive X-axis direction side of the first container 10, thus movement of the dispensing unit 140 can be implemented in a simple configuration, and the installation area of the nucleic acid analyzer 100 can be reduced.

Embodiment 3

Figure 19A:
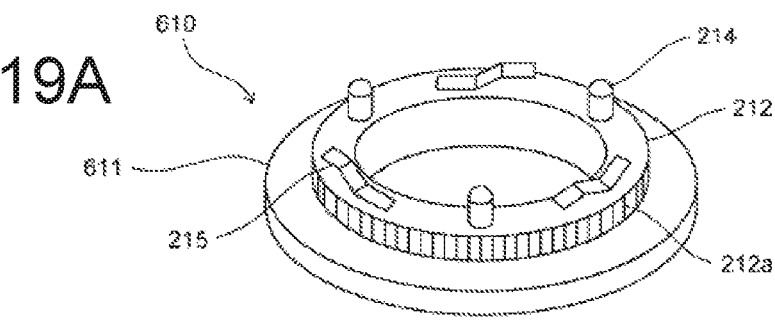
FIGS. 19A to 19C are perspective views schematically illustrating a configuration of a container setting part according to an embodiment 3.
Figure 19B:
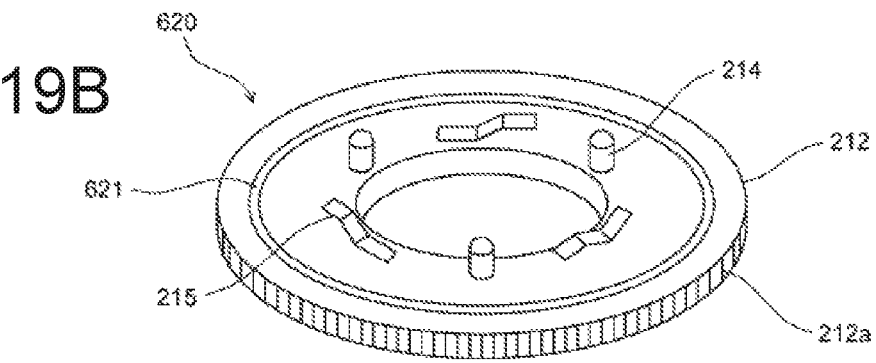
Figure 19C:
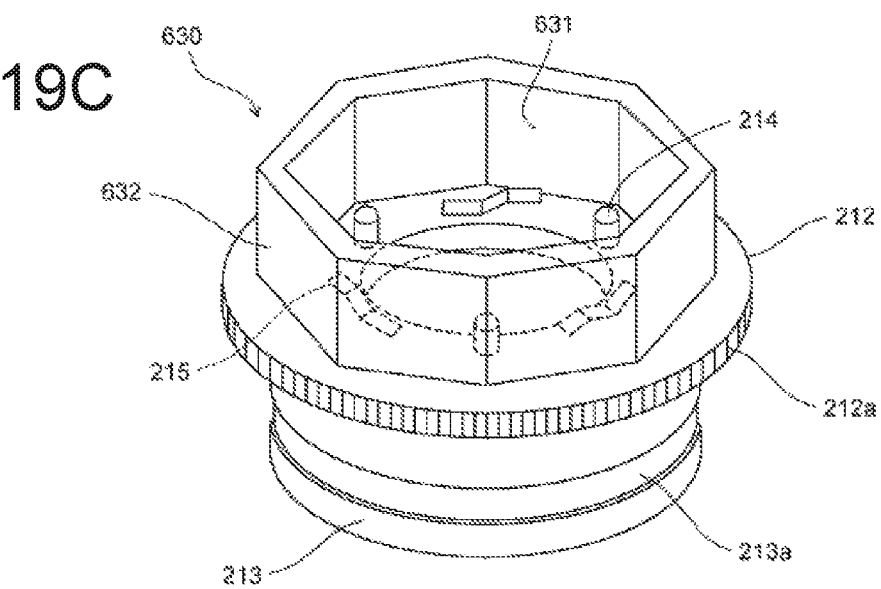

In an embodiment 3, the shape of the container setting part included in the rotation part 200 is the shapes illustrated in FIGS. 19A to 19C.

In a container setting part 610 illustrated in FIG. 19A, as compared with the container setting part 210 in an embodiment 1, the inner-side surface 211 which enclosed three engagement sections 214 is omitted, and a flange section 611 is formed instead of the second outer-side surface 213. In this case, the container setting part 610 is rotatable with fixed positions in a horizontal plane and in the vertical direction using members which hold the flange section 611 from the outside at multiple positions in the circumferential direction instead of using the guide part 250 in an embodiment 1. The container setting part 610 is also formed in a cylindrical shape having openings at the top and bottom, and similarly to an embodiment 1, the second container 20 can be set in the container setting part 610.

In a container setting part 620 illustrated in FIG. 19B, as compared with the container setting part 210 in an embodiment 1, the inner-side surface 211 and the second outer-side surface 213 are omitted, the area in which the engagement sections 214 and the elastic members 215 are provided expands in the outer direction, and a groove 621 is formed in the circumferential direction in the upper surface and the lower surface of the expanded area. In this case, the container setting part 620 is rotatable with fixed positions in a horizontal plane and in the vertical direction using members which vertically hold the groove 621 on the upper surface side and the groove 621 on the lower surface side via balls at multiple positions in the circumferential direction instead of using the guide part 250 in an embodiment 1. The container setting part 620 is also formed in a cylindrical shape having openings at the top and bottom, and similarly to an embodiment 1, the second container 20 can be set in the container setting part 620.

In a container setting part 630 illustrated in FIG. 19C, as compared with the container setting part 210 in an embodiment 1, a cylindrical portion extends upward from the position of each engagement section 214 in the vertical direction. In the cylindrical portion extending upward of the engagement section 214, the sections of the inner-side surface 631 and the outer-side surface 632 taken along a horizontal plane are each a regular octagon. In this case, the second container 20 is also inserted into the cylindrical inner-side surface 631, and set in the container setting part 630.

Embodiment 4

In an embodiment 4, when the second container 20 is rotated at a high speed in the container setting part 210, a float prevention mechanism 700 is used instead of the holding member 330 in order to suppress shaking in the vertical direction of the second container 20.

Figure 20A:
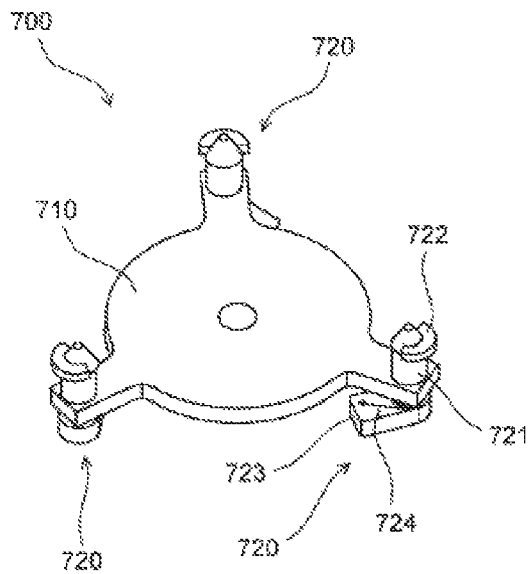
FIGS. 20A to 20D are views schematically illustrating a configuration of a float prevention mechanism according to an embodiment 4.

As illustrated in FIG. 20A, the float prevention mechanism 700 includes a support section 710, and three fasteners 720 set in the support section 710. The three fasteners 720 are disposed at different positions in the circumferential direction of a circle having the center at the central position of the float prevention mechanism 700. Each fastener 720 includes an engagement section 721, a flange section 722, a weight section 723, and a spring 724.

The engagement section 721 is provided on the upper surface side of the support section 710. In the engagement section 721, a shaft (not illustrated) which penetrates through the inside of the engagement section 721 in the vertical direction is rotatably provided in the engagement section 721. The flange section 722 and the weight section 723 are respectively provided on the upper end and the lower end of the shaft of the engagement section 721. The flange section 722 and the weight section 723 extend in a direction in which the sections 722, 723 are away from the shaft of the engagement section 721 in a horizontal plane. Two ends of the spring 724 are provided respectively in the engagement section 721 and the weight section 723. The weight section 723 is urged by the spring 724, and faces the inner side of the float prevention mechanism 700. In this situation, the flange section 722 faces the outer side of the float prevention mechanism 700. The float prevention mechanism 700 is provided inside the container setting part 210 so that the first temperature adjustment part 230 is positioned on the support section 710.

Figure 20B:
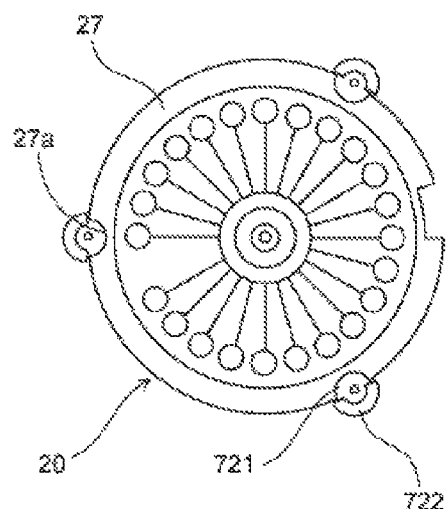

When the second container 20 is set in the container setting part 210 as illustrated in FIG. 20B, three flange sections 722 face the outside due to the spring 724, and thus the second container 20 can be inserted from above the float prevention mechanism 700 without coming into contact with the flange sections 722. Then three engaged sections 27a of the second container 20 are engaged with three engagement sections 721. Consequently, similarly to an embodiment 1, the second container 20 is set in the container setting part 210 with movement in a horizontal plane suppressed.

Figure 20C:
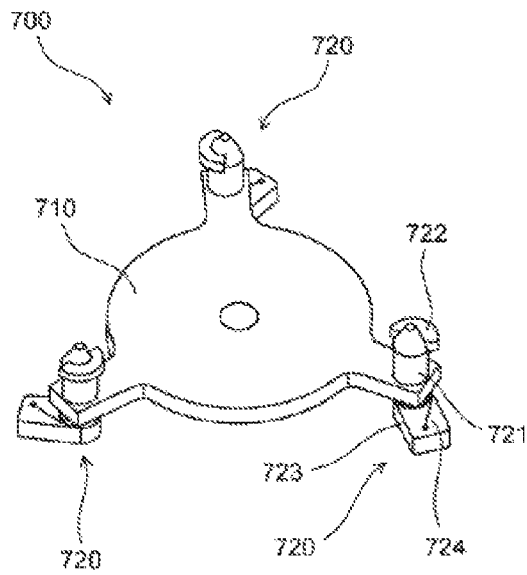
Figure 20D:
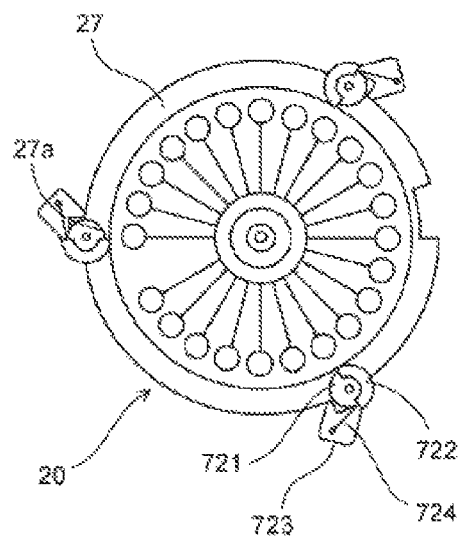

As illustrated in FIG. 20C, when the float prevention mechanism 700 is rotated according to the rotation of the container setting part 210, a centrifugal force is applied to the weight sections 723, thereby causing three weight sections 723 to face the outer side of the float prevention mechanism 700. Thus, the shaft of each engagement section 721 rotates, and the three flange sections 722 rotate. At this point, as illustrated in FIG. 20D, each flange section 722 overlaps with the flange section 27 of the second container 20 in a plan view, thus shaking in the vertical direction of the second container 20 is suppressed.

Embodiment 5

Figure 21A:
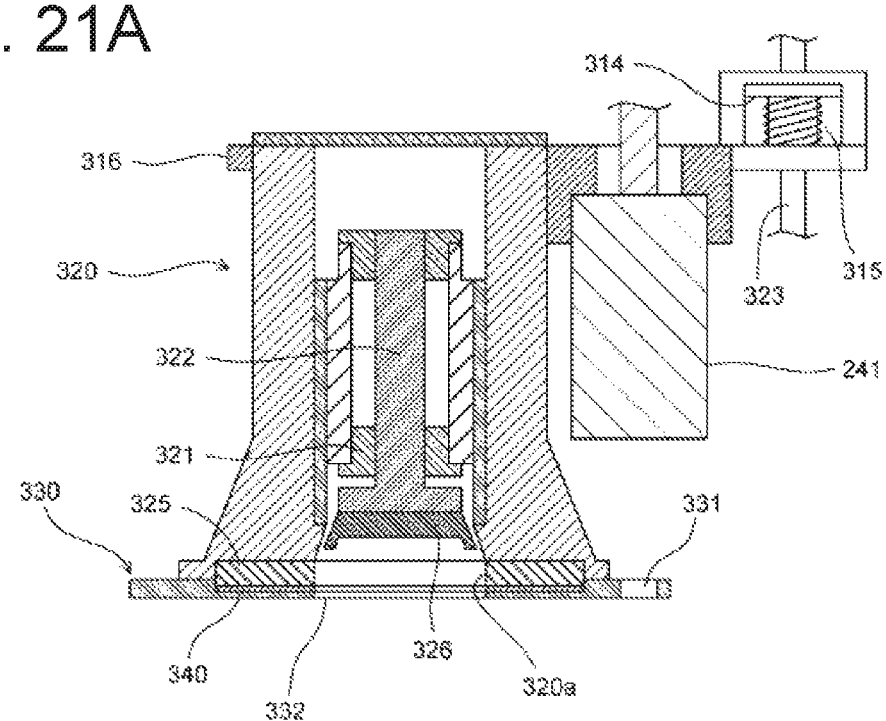
FIG. 21A is a cross-sectional view schematically illustrating a configuration of an urging part according to an embodiment 5.

As illustrated in FIG. 21A, in an embodiment 5, as compared with an embodiment 1, the supporting body 320 includes a receiving member 326 instead of the shaft member 323 and the receiving member 324. Similarly to the receiving member 324 in an embodiment 1, the receiving member 326 is made of fluoro-rubber. The receiving member 326 is provided on the lower surface of the support member 322. The receiving member 326 has a circular shape in a plan view, and the outer circumferential portion of the lower surface extends downward along the inclined surface section 25b of the second container 20.

Figure 21B:
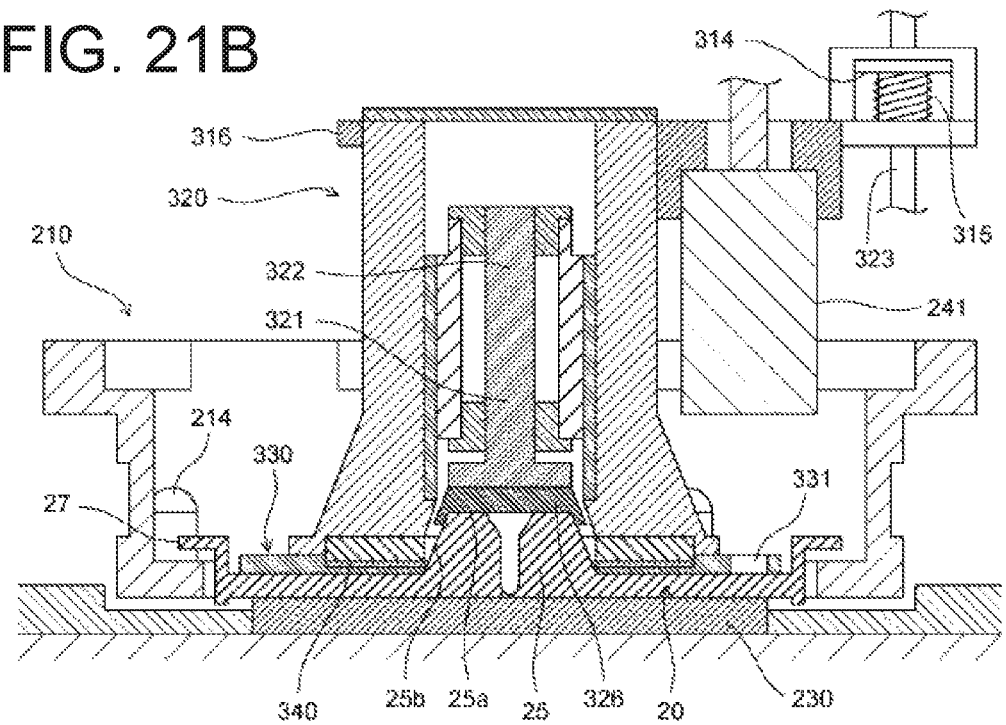
FIG. 21B is a cross-sectional view schematically illustrating a positional relationship between an urging part, a second container, a container setting part, and a first temperature adjustment part when a holding member is positioned at a second position according to an embodiment 5.

As illustrated in FIG. 21B, when the holding member 330 is positioned at the second position, the receiving member 326 fits into the projection 25. Consequently, even when the second container 20 is rotated at a high speed, the upper portion of the injection port 21 is in a state of being sealed by the receiving member 326, thus it is possible to prevent scattering of liquid that flows backward through the injection port 21. In addition, since the receiving member 326 fits into the projection 25, the rotation axis of the second container 20 can also be regulated.

Embodiment 6

Figure 22A:
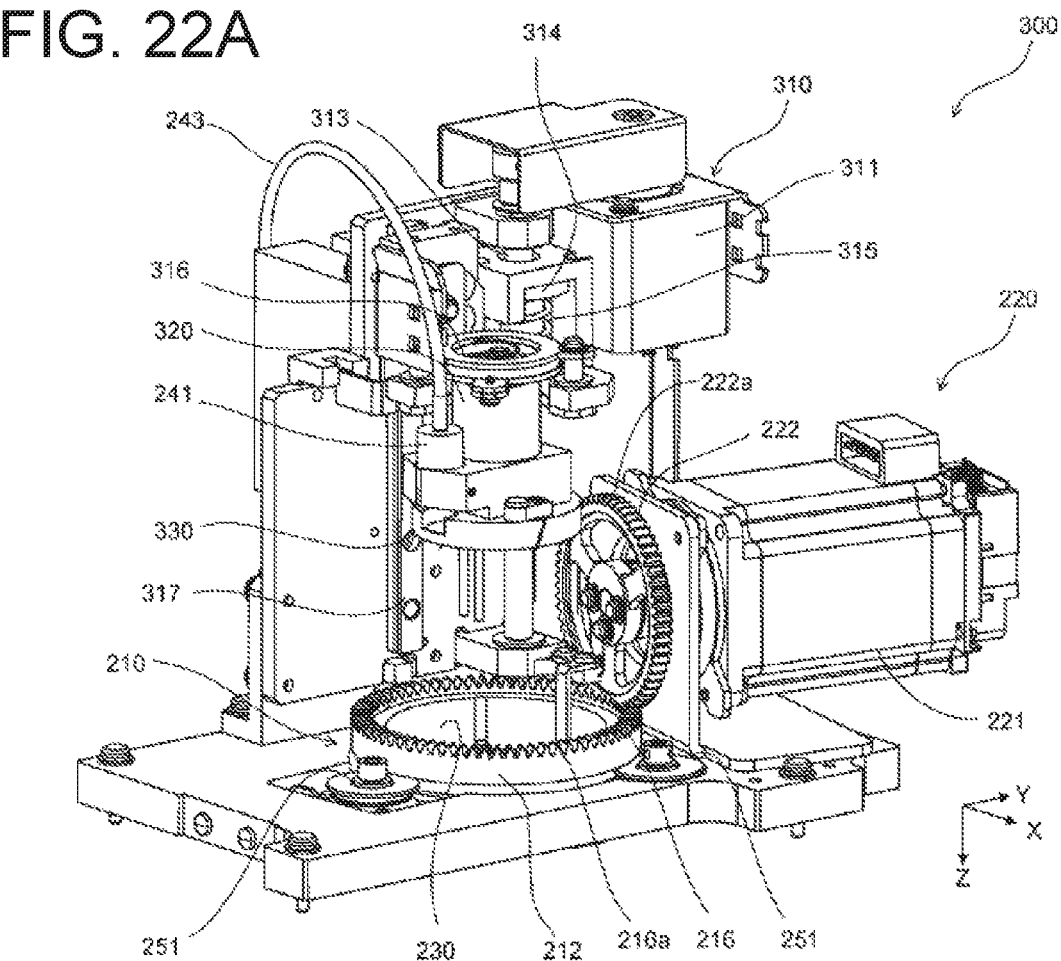
FIG. 22A is a perspective view illustrating a configuration of a rotation part, a detector, and an urging part according to an embodiment 6.

As illustrated in FIG. 22A, in an embodiment 6, the configuration of the rotation drive part 220 is changed, as compared with a first embodiment. Specifically, in an embodiment 1, as illustrated in FIG. 6, a driving force is applied to the first outer-side surface 212 of the container setting part 210, whereas in an embodiment 6, a driving force is applied to an upper surface 216 of the container setting part 210. In an embodiment 6, a gear section 216a is formed on the upper surface 216 of the container setting part 210. The transmission gear 222 connected to a drive shaft 221a of the motor 221 is engaged with the gear section 216a. The motor 221 is installed such that the rotation axis of the drive shaft 221a is parallel to a horizontal plane (X-Y plane). Other configurations of the rotation drive part 220 are the same as those of an embodiment 1 described above.

Figure 22B:
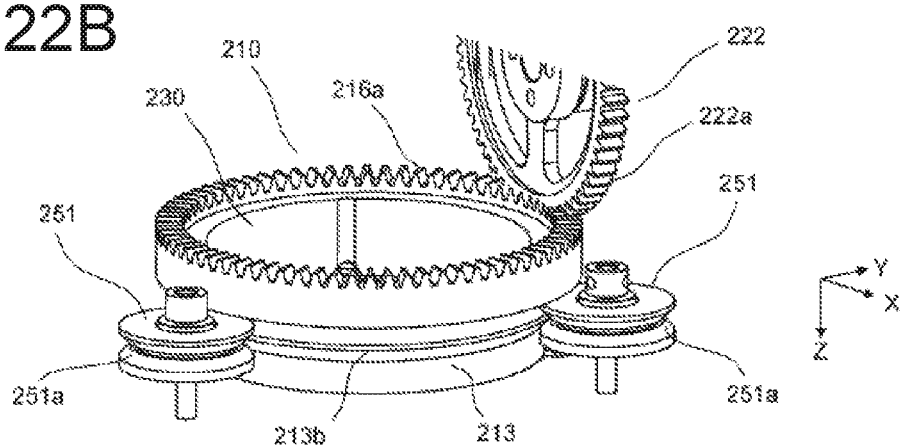
FIG. 22B is a perspective view illustrating a configuration of a container setting part, a rotation drive part, and a guide part according to an embodiment 6.

In an embodiment 6, as illustrated in FIG. 22B, a flange section 213b is formed over the entire circumference of a second outer-side surface 213, and a groove 251a, which is to be engaged with the flange section 213b, is formed over the entire circumference of the outer-side surface of the guide member 251. The container setting part 210 is retained by the engagement of the groove 251a with the flange section 213b. Three guide members 251 are positioned at intervals of 120° when viewed in the positive Z-axis direction. The three guide members 251 are each provided rotatably around an axis parallel to the Z axis direction.

The flange section 213b has a maximum diameter at the central position in the Z-axis direction, and the diameter is smaller at a position away in the positive or negative Z-axis direction from the central position in the Z-axis direction. The flange section 213b has a planar inclined surface on the upper side and the lower side of the central position in the Z-axis direction. On the other hand, the groove 251a of the guide member 251 has a minimum diameter at the central position in the Z-axis direction, and the diameter is larger at a position away in the positive or negative Z-axis direction from the central position in the Z-axis direction. The flange section 213b has a planar inclined surface on the upper side and the lower side of the central position in the Z-axis direction. The guide member 251 is provided with the upper and lower inclined surfaces of the groove 251a in contact with the upper and lower inclined surfaces, respectively, of the flange section 213b.

In an embodiment 6, two inclined surfaces of the groove 251a provided in the guide member 251 receive two inclined surfaces of the flange section 213b provided in the second outer-side surface 213 of the container setting part 210 in this manner, and thus when the container setting part 210 is driven to rotate, vibration of the container setting part 210 in the Z-axis direction can be suppressed. Consequently, noise due to vibration can be suppressed, and a nucleic acid amplification reaction can be smoothly detected without being affected by vibration.

Also, in an embodiment 6, the supporting body 320 and the holding member 330, and the detection head 241 are supported by the support member 316 rotatably in a direction orthogonal to the Z-axis. Consequently, even when the second container 20 is set in the container setting part 210 in a slightly inclined state, the entire upper surface of the second container 20 can be properly held down by the holding member 330.

In addition, in an embodiment 6, the installation position of the detection head 241 in the support member 316 is changed as compared with an embodiment 1. Other configurations in an embodiment 6 are substantially the same as those of an embodiment 1.

Also in the configuration of an embodiment 6, the container setting part 210 can be smoothly rotated. Therefore, a PCR reaction can be properly detected by the second container 20 provided in the container setting part 210.

It is to be noted that in an embodiment 6, the gear section 216*a* is provided in the upper surface 216 of the container setting part 210 to transmit the driving force of the motor 221 to the container setting part 210. However, for instance, when the lower surface side of the container setting part 210 is open, a configuration may be adopted in which the gear section is provided in the lower surface of the container setting part 210 to transmit the driving force of the motor 221 to the container setting part 210.

According to one or more embodiments described above, PCR reaction can be detected in real time with a simple configuration while performing temperature control with high accuracy.

The disclosure includes other embodiments in addition to the above-described embodiments without departing from the spirit of the disclosure. The embodiments are to be considered in all respects as illustrative, and not restrictive. The scope of the disclosure is indicated by the appended claims rather than by the foregoing description. Hence, all configurations including the meaning and range within equivalent arrangements of the claims are intended to be embraced in the description.

What is claimed is:

1. A nucleic acid analyzer that analyzes nucleic acids, comprising:
    a first reaction container holder comprising a first opening configured to hold a reaction container comprising an injection port through which an extraction liquid containing nucleic acids is injected, storages that store reagents for amplifying the nucleic acids, and flow paths connecting the storages and the injection port;
    a second reaction container holder comprising a second opening configured to hold the reaction container containing the extraction liquid injected through the injection port;
    a transport unit configured to detach the reaction container from the first reaction container holder, transport the reaction container from the first reaction container holder to the second reaction container holder, and attach the reaction container to the second reaction container holder;
    a rotation driver comprising a motor and a gear, the rotation driver rotating the reaction container held by the second reaction container holder by generating a driving force by the motor and transmitting the driving force to the reaction container by the gear, to supply the extraction liquid injected through the injection port to the storages through the flow paths by a centrifugal force;
    a first electric heating device provided above or beneath the second reaction container holder and configured to adjust a temperature of the reaction container held by the second reaction container holder, such that a nucleic acid amplification reaction occurs in the storages; and
    a detector provided at a side of the second reaction container holder opposite to the first electric heating device, the detector configured to detect a nucleic acid amplification reaction that occurs in the storages of the reaction container held by the second reaction container holder interposed between the first electric heating device and the detector, wherein
    the detector is arranged movably in a vertical direction so as to be positioned at:
a first position allowing the transport unit to attach the reaction container on the second reaction container holder; and a second position in which the detector approaches the reaction container on the second reaction container holder to perform a detection.

2. The nucleic acid analyzer according to claim 1, wherein
    the second reaction container holder comprises a cylindrical inner-side surface defining a cylindrical space thereby, and
    the reaction container is inserted into the space defined by the cylindrical inner-side surface so as to be held by the second reaction container holder.

3. The nucleic acid analyzer according to claim 1, wherein
    the second reaction container holder comprises a cylindrical first outer-side surface, and
    the rotation driver comprises
        a gear section formed on the first outer-side surface of the second reaction container holder,
        the motor comprising a drive shaft, and
        the gear comprising a transmission gear that connects the drive shaft of the motor and engages the gear section.

4. The nucleic acid analyzer according to claim 1, wherein
    the second reaction container holder comprises a cylindrical second outer-side surface, and
    a guide part that comes into contact with the second outer-side surface to guide the second reaction container holder in rotation.

5. The nucleic acid analyzer according to claim 4, wherein
    a groove with a constant width is formed over an entire circumference of the second outer-side surface, and
    the guide part comprises a guide member provided in the groove.

6. The nucleic acid analyzer according to claim 1, wherein
    the reaction container comprises an engaged section, and
    the second reaction container holder comprises an engagement section which is engaged with the engaged section.

7. The nucleic acid analyzer according to claim 1, further comprising:
    an urging part comprising a spring and disposed on a side of the reaction container held by the second reaction container holder, opposite to the first electric heating device, the urging part configured to urge the reaction container toward the first electric heating device.

8. The nucleic acid analyzer according to claim 7, wherein
    the urging part comprises a holding member comprising a surface capable of coming into contact with the side of the reaction container held by the second reaction container holder, opposite to the first electric heating device, and a movement mechanism that moves the holding member vertically,
    the urging part moves the holding member between the first position at which the holding member comes into contact with the reaction container held by the second reaction container holder to hold down the reaction container, and the second position which is further away from the first electric heating device than the first position and is for regulating movement of the reaction container, the first electric heating device performs temperature adjustment on the reaction container with the holding member positioned at the first position by the urging part, and the rotation driver rotates the reaction container with the holding member positioned at the second position by the urging part.

9. The nucleic acid analyzer according to claim 8, wherein the second reaction container holder comprises an elastic member comprising a spring and configured to keep the reaction container away from the first electric heating device, and the urging part moves the reaction container held by the second reaction container holder in a direction toward the first electric heating device against urging by the elastic member.

10. The nucleic acid analyzer according to claim 9, wherein the urging part moves the holding member to a third position between the first position and the second position, and the detector detects the nucleic acid amplification reaction in the storages of the reaction container with the holding member positioned at the third position.

11. The nucleic acid analyzer according to claim 10, wherein the storages are disposed side by side in a circumferential direction at positions with a constant radius from a rotation center of the reaction container, after the first electric heating device performs temperature adjustment on the reaction container with the holding member positioned at the first position, and the nucleic acid analyzer repeats an operation of the rotation driver to rotate the reaction container in a circumferential direction of the storages with the holding member positioned at the third position, and an operation of the detector to detect the nucleic acid amplification reaction in the storages with the holding member maintained at the third position, to detect the nucleic acid amplification reaction in the storages disposed side by side in the circumferential direction.

12. The nucleic acid analyzer according to claim 11, wherein the first position comprises a position at which the holding member holds the reaction container against the first electric heating device, and the third position comprises a position at which the holding member brings the reaction container into contact with the first electric heating device without holding the reaction container against the first electric heating device.

13. The nucleic acid analyzer according to claim 9, wherein the holding member of the urging part is supported by a support section of the movement mechanism via the spring of the urging part, the urging part moves the support section in a direction toward the first electric heating device, after a surface, facing the first electric heating device, of the reaction container comes into contact with the first electric heating device, and holds the surface of the reaction container against the first electric heating device via the spring.

14. The nucleic acid analyzer according to claim 8, wherein the holding member holds an overlapping area of the storages of the reaction container, and comprises a hole vertically penetrating a position corresponding to the storages, and the detector performs detection on the storages via the hole of the holding member.

15. The nucleic acid analyzer according to claim 8, wherein the detector comprises a detection head facing the storages of the reaction container that irradiates the storages with light to detect the nucleic acid amplification reaction, and an optical unit coupled to the detection head via an optical fiber, the detection head is positioned on the side of the reaction container held by the second reaction container holder, opposite to the first electric heating device, and the detection head is supported by a support member that supports and vertically moves the holding member.

16. The nucleic acid analyzer according to claim 7, wherein the urging part comprises a shaft regulation part that is engaged with the reaction container held by the second reaction container holder, and regulates a rotation axis of the reaction container.

17. The nucleic acid analyzer according to claim 16, wherein the shaft regulation part comprises a shaft member that is fitted in the injection port of the reaction container.

18. The nucleic acid analyzer according to claim 16, wherein the reaction container comprises an axially symmetric projection comprising the injection port and a reduced thickness toward an end thereof, and the shaft regulation part comprises a receiving member in which the projection is fitted.

19. The nucleic acid analyzer according to claim 7, wherein the urging part comprises a second electric heating device that adjusts a temperature of the reaction container in the second reaction container holder.

20. A nucleic acid analyzing method comprising:

positioning a reaction container on a first reaction container holder, the reaction container comprising an injection port through which an extraction liquid containing nucleic acids is injected, storages that store reagents for amplifying the nucleic acids, and flow paths connecting the storages and the injection port;

injecting the extraction liquid to the reaction container on the first reaction container holder through the injection port;

transporting the reaction container to a second reaction container holder from the first reaction container holder;

rotating the reaction container on the second reaction container holder by a driving force, to supply the extraction liquid injected through the injection port to the storages through the flow paths by a centrifugal force;

adjusting a temperature of the reaction container on the second reaction container holder by an electric heating device disposed on either of upper and lower sides of the second reaction container holder, such that a nucleic acid amplification reaction occurs in the storages; and detecting, during the rotating, the nucleic acid amplification reaction by a detector disposed on the other side of the upper and lower sides of the second reaction container holder, wherein the detector is arranged movably in a vertical direction so as to be positioned at:

a first position allowing the reaction container to be attached on the second reaction container holder; and a second position in which the detector approaches the reaction container on the second reaction container holder to perform a detection.

* * * * *